United States Patent
O'Connor et al.

(10) Patent No.: US 11,135,231 B2
(45) Date of Patent: Oct. 5, 2021

(54) METHODS AND COMPOSITIONS FOR PREVENTION AND TREATMENT OF APICOMPLEXAN INFECTIONS

(71) Applicants: Tufts Medical Center, Inc., Boston, MA (US); Washington State University, Pullman, WA (US); University of Utah Research Foundation, Salt Lake City, UT (US)

(72) Inventors: Roberta O'Connor, Pullman, WA (US); Eric W. Schmidt, Salt Lake City, UT (US)

(73) Assignees: Washington State University, Pullman, WA (US); Tufts Medical Center, Inc., Boston, MA (US); University of Utah, Salt Lake City, UT (US)

( * ) Notice: Subject to any disclaimer, the term of this patent is extended or adjusted under 35 U.S.C. 154(b) by 162 days.

(21) Appl. No.: 16/467,320

(22) PCT Filed: Dec. 7, 2017

(86) PCT No.: PCT/US2017/065189
§ 371 (c)(1),
(2) Date: Jun. 6, 2019

(87) PCT Pub. No.: WO2018/106966
PCT Pub. Date: Jun. 14, 2018

(65) Prior Publication Data
US 2020/0306276 A1     Oct. 1, 2020

Related U.S. Application Data

(60) Provisional application No. 62/431,210, filed on Dec. 7, 2016.

(51) Int. Cl.
| | |
|---|---|
| *A61K 31/365* | (2006.01) |
| *A61K 31/69* | (2006.01) |
| *A61P 33/06* | (2006.01) |
| *A61K 45/06* | (2006.01) |

(52) U.S. Cl.
CPC .............. *A61K 31/69* (2013.01); *A61K 45/06* (2013.01); *A61P 33/06* (2018.01)

(58) Field of Classification Search
CPC ........ A61K 31/365; A61K 31/69; A61P 33/00
USPC .................................................. 514/450, 449
See application file for complete search history.

(56) References Cited

FOREIGN PATENT DOCUMENTS

DE          4313990 A1      11/1994

OTHER PUBLICATIONS

S. Elshahawi et al. "Boronated tartrolon antibiotic produced by symbiotic cellulose-degrading bacteria in shipworm gills," Proceedings National Academy of Sciences, Jan. 3, 2013, vol. 110, No. 4, pp. E295-E304.
M. Perez et al. "Tartrolon D, a Cytotoxic Macrodiolide from the Marine-Derived Actinomycete *Streptomyces* sp. MDG-04-17-069," Journal of Natrual Products, Dec. 28, 2009, vol. 72, No. 12, pp. 2192-2194.
J. Solecka et al. "Biologically active secondary metabolites from Actinomycetes," Central European Journal of Biology, Jun. 2012, vol. 7, No. 3, pp. 373-390.
ISA/EPO, "International Search Report" and "Written Opinion of the International Searching Authority," PCT/US2017/065189, dated Mar. 28, 2018.
J. Mead "Cryptosporidiosis and the challenges of chemotherapy," Drug Resistance Updates, Mar. 2002, vol. 5, pp. 47-57.
A. Armson et al. "A review of chemotherapeutic approaches to the treatment of cryptosporidiosis," Expert Rev. Anti Infect. Ther., 2003, vol. 1, No. 2, pp. 297-305.
W. Checkley et al. "A review of the global burden, novel diagnostics, therapeutics, and vaccine targets for cryptosporidium," Lancet Infect. Dis., Jan. 2015, vol. 15, No. 1, pp. 85-94.

*Primary Examiner* — Charanjit Aulakh
(74) *Attorney, Agent, or Firm* — Milstein Zhang & Wu LLC; Duan Wu, Esq.

(57) ABSTRACT

Methods and compositions for preventing and/or treating diseases and conditions caused by certain apicomplexan infections are provided. The methods involve administering/providing to a subject one or more of tartrolon D and E, including isomers thereof. Exemplary apicomplexan infections that are prevented/treated by the compounds of the invention include those caused by *Cryptosporidium, Babesia, Cyclospora, Isospora, Plasmodium, Sarcocystis, Besnoitia, Hammondia, Neospora, Theileria* and *Toxoplasma*.

18 Claims, 17 Drawing Sheets
(8 of 17 Drawing Sheet(s) Filed in Color)

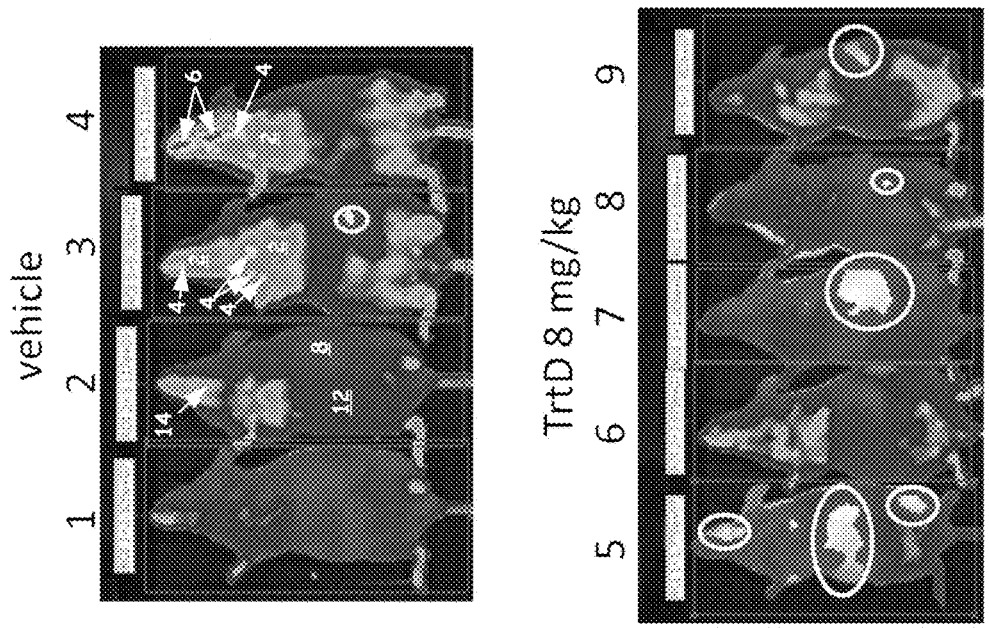
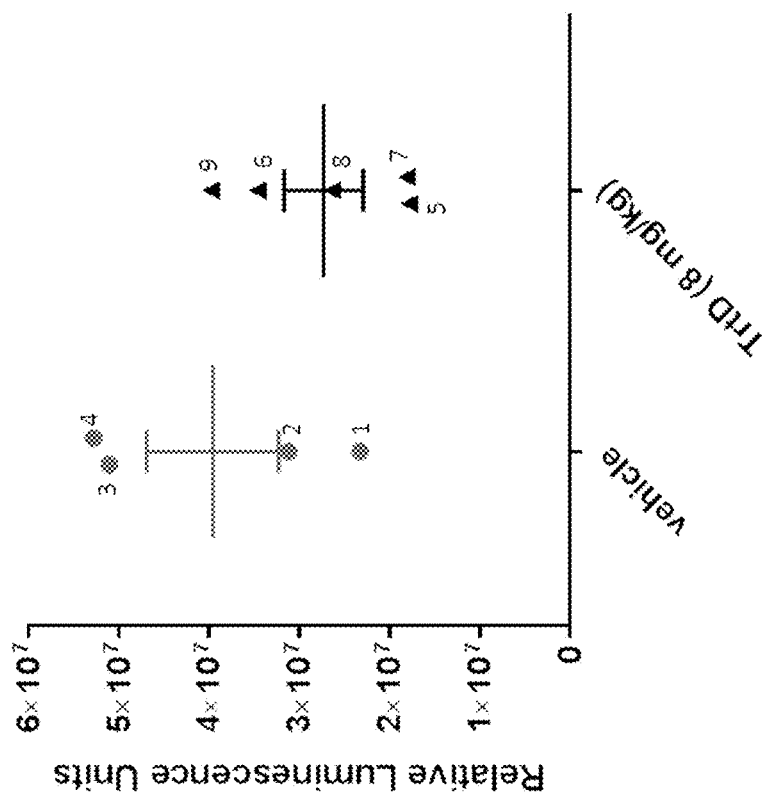
FIG. 14B
FIG. 14A

METHODS AND COMPOSITIONS FOR PREVENTION AND TREATMENT OF APICOMPLEXAN INFECTIONS

CROSS-REFERENCE TO RELATED APPLICATIONS

This application is a national phase application under 35 U.S.C. 371 of international application PCT/US2017/065189, filed Dec. 7, 2017 which claims priority to and the benefit of U.S. provisional patent application Ser. No. 62/431,210, filed Dec. 7, 2016, which application is incorporated herein by reference in its entirety.

STATEMENT REGARDING FEDERALLY SPONSORED RESEARCH OR DEVELOPMENT

The invention was made with government support under grants AT009174 and TW008163 awarded by the National Institute of Health. The government has certain rights in the invention.

FIELD OF THE INVENTION

The invention generally relates to methods and compositions for preventing and treating diseases and conditions caused by certain Apicomplexan infections. In particular aspects, the invention provides methods and compositions for preventing and treating diseases and conditions caused by *Cryptosporidium, Babesia, Cyclospora, Isospora, Plasmodium, Sarcocystis, Theileria, Besnoitia, Neospora, Hammondia* and *Toxoplasma* by administering one or more tartrolons to an infected or susceptible subject.

BACKGROUND OF THE INVENTION

The phylum of Apicomplexa, also called Apicomplexia, include a large group of parasitic protozoan alveolates such as the coccidia, gregarines, piroplasms, and haemosporidia. These organisms are spore-forming, and most species are obligate intracellular parasites of animals. After penetrating into host cells and causing infection, members of the Apicomplexa can cause diseases that affect both humans and other animals including farm animals and pets. Apicomplexan infections cause diseases that are of great importance, both economically and due to the resulting suffering. These diseases include: cryptosporidiosis (by a *Cryptosporidium* species, e.g., *C. hominis* and *C. parvum*), toxoplasmosis (by *Toxoplasma gondii*), babesiosis (by a *Babesia* species), malaria (by a *Plasmodium* species), cyclosporiasis (by *Cyclospora cayetanensis*), isosporiasis (by a *Isospora* species, e.g., *Isospora belli*), theileriosis (by a *Theileria* species), sarcocystosis (by a *Sarcocystis* species), besnoitiosis (by a *Besnoitia* sp.), hammondiaiasis (by a *Hammondia* sp.), neosporiasis (by a *Neospora* sp.) and others. Animals affected by various apicomplexan infections include: horse, sheep, goat, bovine, chicken, turkey, duck, goose, dog, cat, pig, rabbit, donkey, camelids (e.g., camels, llamas, alpaca), kangaroo, wallaby, lemur, birds, penguin, sea lion, seal, sea mammals like otter, and so on.

Amongst Apicomplexan infections, cryptosporidiosis is the most common cause of parasitic diarrhea in the developing world (Ajjampur S S, et al. (2008) *J Med Microbiol* 57(Pt 11): 1364-1368). Cryptosporidiosis causes growth and developmental delays in young children (Duong T H, et al. (1995) *Sante* 5(3):185-188), even when the infection is asymptomatic (Checkley W, et al. (1997) *Am J Epidemiol* 145(2):156-163). A recent analysis of the burden of cryptosporidiosis in sub-Saharan Africa and southern Asian countries estimated 7.6 million cases of cryptosporidiosis per year in children under 2 years old, with 202,000 deaths attributable to this pathogen (Sow S O, et al. (2016) *PLoS Negl Trop Dis* 10(5):e0004729). This analysis does not take into account the morbidity resulting from repeated asymptomatic infections experienced by children in endemic areas.

*Cryptosporidium* species are ubiquitous in industrialized countries as well. In 2007, *Cryptosporidium* was identified as the cause of 87% of waterborne illnesses in the US (Hlaysa M C, et al. (2011) *MMWR Surveill Summ* 60(12): 1-32). In 1993, contamination of the Milwaukee's water supply led to over 400,000 cases of cryptosporidiosis, resulting in 69 deaths (Mac Kenzie W R, et al. (1994) *N Engl J Med* 331(3):161-167). *Cryptosporidium parvum* is also a common cause of scours in dairy herds, especially neonatal calves, often bringing large economic losses to inflicted farms. Bovine babesiosis is another disease that can cause havoc in cattle populations.

In recognition of its potential as a biological weapon, *Cryptosporidium* is classified by the CDC and NIH as a Category B agent. Clearly, development of an effective therapeutic for treatment of cryptosporidiosis is a medical and public health imperative. Currently, there are no drugs available to cure cryptosporidiosis in immunocompromised patients (Abubakar I, et al. (2007) *Cochrane Database Syst Rev* 1:CD004932). There is only one drug available to treat the disease in immunocompetent patients: nitazoxinide, and its efficacy in controlling and treating cryptosporidiosis leaves much to be desired.

Another disease caused by an apicomplexan parasite is the well-known disease of malaria, which affects both humans and other animals. Malaria is most commonly transmitted by infected mosquitos when their bites introduce the apicomplexan parasite *Plasmodium* into the host. Widespread in the tropical and subtropical regions including Sub-Saharan Africa, Asia, and Latin America, malaria still exacts a large toll on human and animal lives: in 2015, there were 296 million human cases of malaria worldwide with an estimated 731,000 deaths. According to a 2005 study, economic losses from malaria in Africa alone were estimated to be US$12 billion a year. Greenwood et al. (2005) *Lancet* 365(9469): 1487-1498. In human, malaria is caused by five species of *Plasmodium: P. falciparum, P. malariae, P. ovale, P. vivax* and *P. knowlesi*. Among human cases, *P. falciparum*, account for about 75% of the infection and the most deaths. While there are antimalarial treatments, drug resistance is now common against all classes of antimalarial drugs except for artemisinins—and with confirmation of *P. falciparum* strains resistant to artemisinins in several Southeast Asian countries, there is dire urgency to develop new and effective treatment against malaria-causing *Plasmodium*. Sinha et al. (2014) *Parasite* 21:61. Moreover, besides *Plasmodium*, most other apicomplexans are also quick to develop drug resistance; therefore, discovery of new, effective drugs is always a medical and veterinary imperative.

Therefore, there is a strong need for therapeutics and prophylactics that can effectively control and treat veterinary and human diseases caused by *Cryptosporidium parvum*, *Plasmodium falciparum*, and other apicomplexan parasites.

SUMMARY OF THE INVENTION

Provided herein are methods and compositions for preventing and/or treating diseases and unwanted conditions caused by one or more protozoan parasites of the Apicomplexa phylum. The methods generally involve administering to a subject in need thereof a therapeutically effective amount of one or more of the macrodioloide polyketides tartrolon D, its boronated derivative tartrolon E, and stereoisomers thereof ("compounds of the invention"). When contacted with or exposed to at least one of the compounds of the invention, apicomplexan parasites are irreversibly inhibited or killed. Thus, the present disclosure also provides methods of inhibiting or killing certain protozoan parasites of the Apicomplexa phylum by contacting the parasites with or exposing the parasites to an amount of at least one of tartrolon D and tartrolon E (or therapeutically active stereoisomers thereof), exposure being in an amount sufficient to kill or damage the parasites, thereby preventing (prophylactically treating) or treating therapeutically infections caused by the parasites. The parasites may be in vivo (e.g., present in an infected host, a host that is susceptible to infection, or an intermediary organism), ex vivo (e.g., on a surface or in an area that may foster contact between the parasite and a potential host organism, or in a parasite habitat), or in a vector that transmits the parasite to a host (e.g., in a vector habitat).

In one aspect, the present invention relates to a method of treating or preventing a disease caused by an apicomplexan parasite in a subject in need thereof. The method comprises administering to the subject tartrolon D, tartrolon E or both, i.e., at least one of tartrolon D and E, in an amount that is therapeutically effective to inhibit or kill the apicomplexan parasite. In one feature, the tartrolon D or E or both have been isolated or purified, e.g., from a population of the bacteria, *Teredinibacter turnerae*, preferably the strain T7901. In an embodiment, the subject is administered tartrolon D or E or both in a dose of at least about 2 mg for every kg of the subject's weight. In one feature, the subject is administered a second anti-parasitic agent against the same or related parasite. The subject may be selected from the group consisting of human, horse, sheep, goat, bovine, chicken, turkey, duck, goose, dog, cat, pig, rabbit, donkey, camelids (e.g., camels, llamas, alpaca), kangaroo, wallaby, lemur, birds, sea lion, seal, and sea otter.

In another aspect, the present invention provides a pharmaceutical composition comprising: (a) substantially isolated or purified tartrolon D, tartrolon E or both, i.e., at least one of tartrolon D and E, in an amount that is therapeutically effective against an apicomplexan parasite; and (b) a pharmaceutically acceptable excipient, carrier, or diluent. In a feature, the composition further includes (c) a second anti-parasitic agent against the same or related parasite. In one embodiment, the composition further includes an agent selected from the group consisting of an antibiotic, anti-protozoan agent, adjuvants and a chemotherapeutic agent.

In yet another aspect, the present invention provides a food supplement comprising tartrolon D, tartrolon E or both, in a concentration effective to inhibit a disease caused by an apicomplexan parasite. In some embodiments, the food supplement is an animal feed, e.g., one made to feed cattle, horse or goat. In another embodiment, the food supplement of the present invention is safe for human consumption.

In various embodiments, the apicomplexan parasite being targeted by the compounds of the invention is a *Cryptosporidium* (e.g., *C. parvum*, or *C. hominis*), *Toxoplasma* (e.g., *T. gondii*), *Babesia* species (e.g., *B. bovis*), or *Plasmodium* species (e.g., *P. falciparum*, or *P. malariae*). In other embodiments, the apicomplexan parasite is selected from the group consisting of *Cyclospora, Isospora, Sarcocystis, Theileria, Besnoitia, Hammondia,* and *Neospora*.

In one feature, the disease being treated by the compounds of the invention is cryptosporidiosis, toxoplasmosis, babesiosis, malaria, cyclosporiasis, isosporiasis, sarcocystosis, or theileriosis (also known as East Coast fever).

In another feature, the second anti-parasitic agent to be added to or used in combination with the compounds of the invention is selected from the group consisting of nitazoxinide, atovaquone, proguanil, artimisinin, piperaquine, chloroquine, mefloquine, doxycycline, amodiaquine, lumefantrine, sulfadoxine/pyrimethamine, quinine and clindamycin, primaquine, and tafenoquine.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

The patent or application file contains at least one drawing executed in color. Copies of this patent or patent application publication with color drawings will be provided by the Office upon request and payment of the necessary fee.

The objects and features of the invention can be better understood with reference to the drawings described below, and the claims. The drawings are not necessarily to scale, emphasis instead generally being placed upon illustrating the principles of the invention.

FIG. 3A is a HPLC chromatogram comparison between purified sample in Example 2 and previously reported tartrolon D. FIG. 3B shows mass spectrometry data of the sample from Example 2. FIG. 3C shows NMR data of the sample from Example 2.

FIGS. 14A and 14B illustrates in vivo data showing that the compound(s) of the invention substantially reduce *Plasmodium berghei* infection in neonatal mice: (14A) graphically represents relative luminescence units emitted by nine mice sacrificed; and (14B) shows the fluorescent image of each of the same nine mice produced by the IVIS lumina.

DETAILED DESCRIPTION OF THE INVENTION

Figure 1:
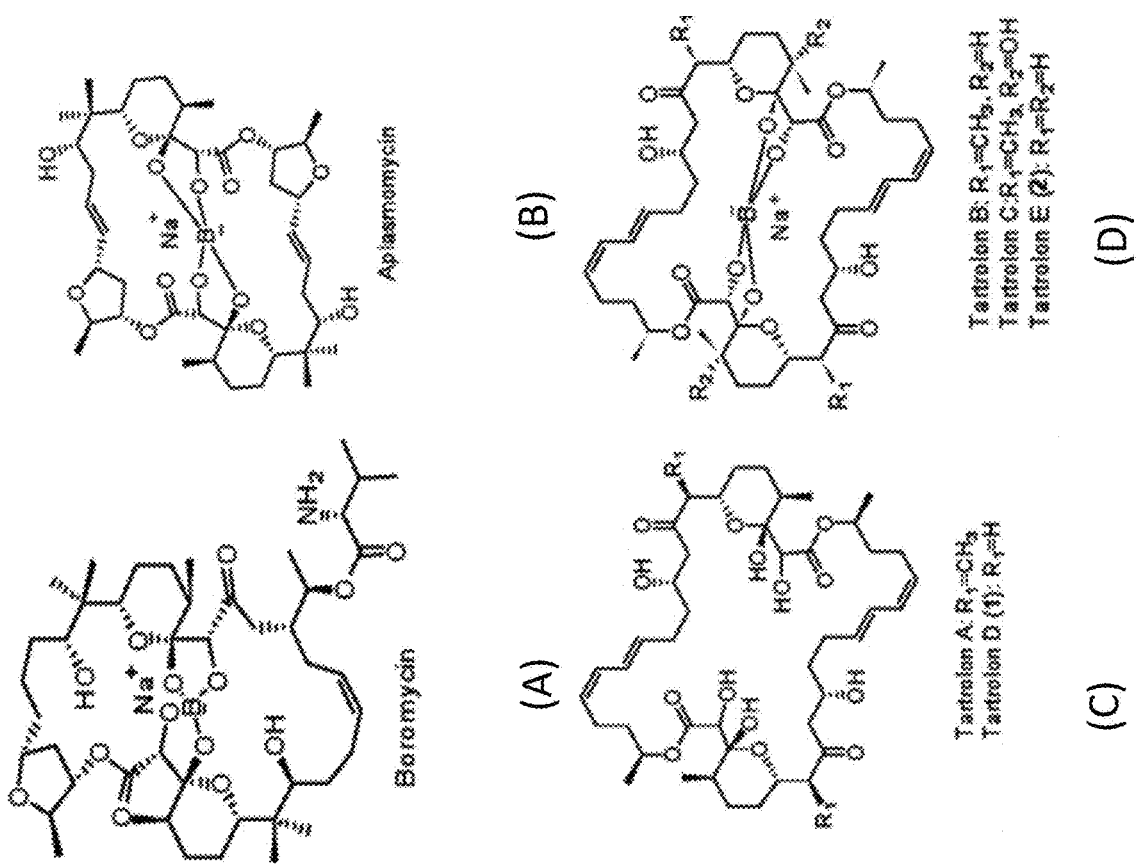
FIG. 1 illustrates the chemical structures of the tartrolons and related compounds, which are all macrodiolides: (A) boromycin; (B) aplasmomycin; (C) tartrolon A where $R_1$ is $CH_3$, and tartrolon D where $R_1$ is H; and (D) tartrolon B, tartrolon C, and tartrolon E.

Unless otherwise noted, technical terms are used according to conventional usage. Definitions of common terms in molecular biology may be found, for example, in J. Krebs et al. (eds.), *Lewin's Genes XII*, published by Jones and Bartlett Learning, 2017 (ISBN 9781284104493); Robert A. Meyers (ed.), *Molecular Biology and Biotechnology: a Comprehensive Desk Reference*, published by Anmol Publications Pvt. Ltd, 2011 (ISBN 9788126531783); and other similar technical references.

As used in the specification and claims, the singular form "a", "an", or "the" includes plural references unless the context clearly dictates otherwise. For example, the term "a cell" includes a plurality of cells including mixtures thereof. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent," or "except for [a particular feature or element]," or "wherein [a particular feature or element] is not present (included, etc.) . . . ".

The term "isolated" or "purified" as used herein refers to a material that is substantially or essentially free from components that normally accompany it in its native state. Purity and homogeneity are typically determined using analytical chemistry techniques such as polyacrylamide gel electrophoresis or high performance liquid chromatography.

As used herein, the terms "treat", "treating", and "treatment" have their ordinary and customary meanings, and include one or more of: blocking, ameliorating, or decreasing in severity and/or frequency a symptom of a disease or condition (e.g., infection) in a subject, and/or inhibiting the growth, division, spread, or proliferation of an infectious agent or pathogen in a subject. Treatment means blocking, ameliorating, decreasing, or inhibiting by about 10% to about 100% versus a subject in which the methods of the present invention have not been practiced. Preferably, the blocking, ameliorating, decreasing, or inhibiting is about 100%, 99%, 98%, 97%, 96%, 95%, 90%, 80%, 70%, 60%, 50%, 40%, 30%, 20%, or 10% versus a subject in which the methods of the present invention have not been practiced. Treatment can be for an existing condition or prophylactically for future conditions.

As described herein, it has now been discovered that polyketide metabolites, tartrolon D and/or its boronated derivative tartrolon E, in the form of various stereoisomers or epimers (individually or collectively referred to as the "compound of the invention", "compounds of the invention", or "compound(s) of the invention" and sometimes referred to as "tartrolon D/E"), have anti-parasitic properties, i.e., they inhibit and/or kill apicomplexan parasites in vitro, ex vivo and in vivo. Accordingly, disclosed herein is the use of tartrolons D and E, stereoisomers/epimers thereof, and mixtures thereof, for the prevention, treatment, and/or the reduction of symptoms of infections caused by certain protozoan parasites of the Apicomplexa phylum. In particular, what is prevented or treated are infections caused by species of the genera of *Cryptosporidium, Babesia, Cyclospora, Isospora, Plasmodium, Sarcocystis, Theileria, Besnoitia, Hammondia, Neospora* and *Toxoplasma*.

The compound(s) of the invention may be purified from a culture of the shipworm symbiotic bacteria, *Teredinibacter turnerae*, or synthesized, either chemically or using recombinant genetic technologies.

For therapeutic purposes, the compounds of the invention may be formulated into a pharmaceutical composition, by mixing a therapeutically effective amount of the compound(s) of the invention with a pharmaceutically acceptable excipient, carrier, or diluent, and optionally in combination with one or more additional active agents, e.g., a second anti-parasitic agent. The "half maximum effective concentration" ($EC_{50}$), the concentration that produces a half-maximal (50%) response, by tartrolon D/E was generally in the range of 0.1-16 nM against the apicomplexan parasites tested. With an $EC_{50}$ value as low as the picomolar to nanomolar level provides further confidence that the active ingredients, once administered in vivo, would likely achieve the expected anti-parasitic effects. According to an aspect of the present invention, tartrolon D and/or tartrolon E can be used as a therapeutic for treatment or prevention of human and animal diseases caused by various protozoan parasites.

Compounds of the Invention

Compounds which may be used in the practice of the invention include but are not limited to tartrolon D, depicted in Formula I:

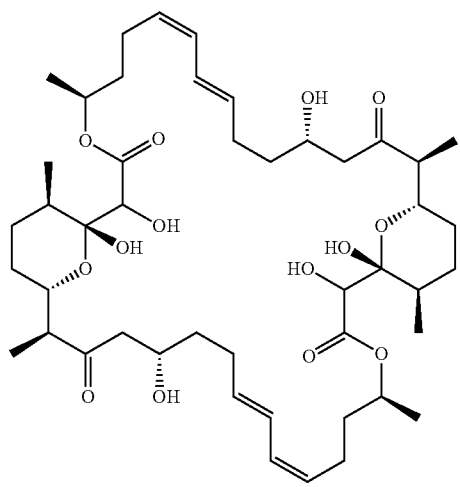

(I)

and/or tartrolon E, depicted in Formula II:

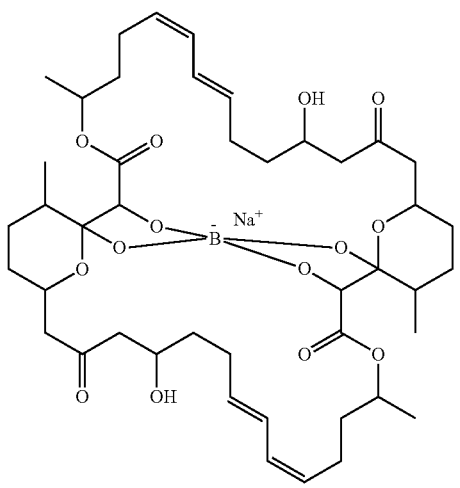

(II)

and are meant to include stereoisomers/epimers of tartrolons D and E.

Little is known on the tartrolons and related compounds (FIGS. 1A-1D). One of these compounds, boromycin (FIG. 1A), was reportedly added to chicken feed to prevent the development of *Eimeria* infections (Rezanka T & Sigler K (2008) *Phytochemistry* 69(3):585-606), which are coccidian parasites closely related to *Cryptosporidium* that cause severe gastrointestinal pathology in poultry. Aplasmomycin (FIG. 1B), another related compound (Nakamura H, et al. (1977) *J Antibiot* (Tokyo) 30(9):714-719), was so named for its activity against *Plasmodium*, both in vitro and in vivo (Balu N, et al. (1991) *Journal of Medicinal Chemistry* 34(9):2821-2823; Okami Y, et al. (1976) *J Antibiot* (Tokyo) 29(10): 1019-1025). In particular, monoterpenic fragment analogues of aplasmomycin were reported to espouse antimalarial activities in vitro (Biswas S, et al. (1995) *Indian Journal of Experimental Biology* 33(7):521-523). The broad range of in vitro and in vivo data on anti-apicomplexan activities presented herein shows that tartrolon D/E are active and effective anti-parasitic agents.

Tartrolon D consists of two polyketide chains joined as diesters. It was initially isolated from *Streptomyces* sp. MDG-04-17-069 fermentation broths and displayed strong cytotoxic activity against three human tumor cell lines (Pérez, M et al. (2009) *J. Nat. Prod.* 72(12):2192-2194). More recently, tartrolon D and its boronated derivative tartrolon E were reported to exhibit antibacterial properties (Elshahawi, S et al. (2013) *PNAS USA* 110(4):E295-E304). We report here discovery of anti-parasitic properties in tartrolon D and E for the first time.

Tartrolon D converts into Tartrolon E in the presence of borate. Tartrolon E can convert into Tartrolon D by addition of acid. The two are generally in equilibrium in a solution. The two Tartrolons have three stereoisomers (epimers) depending on the orientation of the —OH groups shown with dotted line bonds in the structures above, the three epimers have: both —OH groups up, both —OH groups down, and one —OH group up and one —OH group down. Our results show that different epimers have similar if not identical inhibitory effects on apicomplexan growth. Also shown below is that Tartrolon D and Tartrolon E also have similar if not identical inhibitory effects on apicomplexan growth. This may be because in biological media borate is generally present and this may cause Tartrolon D to convert to Tartrolon E in biological media or biological systems, resulting in a mixture of Tartrolons D and E. Our results show that Tartrolon D and Tartrolon E, and their three epimers have similar if not identical inhibitory effects on apicomplexan growth. As used herein, the symbol Tartrolon "D/E" is used to mean either Tartrolon D or Tartrolon E, or any of their three respective epimers, or mixtures of all the above. All are similarly, comparably or identically inhibitory to apicomplexan growth.

Making Compounds of the Invention

Shipworms are marine bivalves that survive by borrowing into and consuming wood, a lifestyle entirely enabled by their symbiotic bacteria (Distel D L (2003) "The biology of marine boring bivalves and their bacterial endosymbionts," *Wood Deterioration and Preservation*, eds. Goodell B, Nicholas D, & Schultz T (American Chemical Society Press, Washington, D.C.), pp 253-271). Shipworm's symbionts reside within specialized cells (bacteriocytes) of the gill (Distel D L, et al. (1991) *Appl Environ Microbiol* 57(8): 2376-2382). These intracellular γ-proteobacteria accomplish three tasks that are responsible for the shipworm's success: they produce lignocelluolytic enzymes that are selectively transported out of the bacterial vacuole, out of the bacteriocyte, out of the gill and to the lumen of the digestive tract to digest wood (O'Connor R M, et al. (2014) *PNAS USA* 111(47):E5096-E5104); they fix atmospheric nitrogen to supplement this protein-poor diet (Lechene C P et al. (2007) *Science* 317(5844):1563-1566); and they produce secondary metabolites with potent anti-bacterial activity (Trindade-Silva A E, et al. (2009) *Genet Mol Biol* 32(3):572-581). Analysis of the genomes of shipworm symbionts reveals a significant commitment to the production of polyketide and non-ribosomal peptide secondary metabolites, including loci with mixed polyketide-non-ribosomal peptide synthase domains (Elshahawi S, et al. (2012) "Isolation and Biosynthesis of Bioactive Natural Products by Marine Symbionts" *Scholar Archive Paper* 794; Yang J C, et al. (2009) *PloS one* 4(7):e6085), suggesting the potential to produce chemically complex and unique bioactive compounds.

The compound(s) of the invention, in one exemplary embodiment, is produced by a cultured population of one of the shipworm's symbiotic bacteria, *Teredinibacter turnerae*. Effective amounts of the compounds of the invention can be found and purified from both culture supernatant and cell lysate where the growth medium provides a source of boron (see Examples below).

*T. turnerae* is a species of shipworm gill symbiont found in almost all species of shipworm (Distel D L et al. (2002) *Int J Syst Evol Microbiol* 52(Pt 6):2261-2269). *T. turnerae* is a cellulolytic, microaerophilic, nitrogen-fixing gamma proteobacterium easily propagated in a broth consisting predominantly of seawater and a carbon source such as sucrose or cellulose. Many strains of *T. turnerae* have been isolated and sequenced (see Joint Genome Institutes IMG database for *T. turnerae* sequences T7901, T7902, T8402, T8412, T8415, T8513, T8602, T0609, 1675L.s.0a.01, 1133Y.S.0a.04, 991H.S.0a.06, 1162T.S.0a.05). The genome of *T. turnerae* strain T7901 (hereinafter sometimes referred to as "T7901") has been published (Yang J C, et al. (2009) *PloS one* 4(7):e6085). The T7901 genome encodes 9 secondary metabolite gene clusters. The small molecule products of two of these gene clusters have been identified and characterized (Han A W, et al. (2013) *PloS one* 8(10): e76151). Among them, Cluster 2 encodes the enzymes that produce the polyketide tartrolon D, and its boronated derivative, tartrolon E (Elshahawi, S et al. (2013) *PNAS USA* 110(4):E295-E304). Many strains of *T. turnerae* can produce tartrolon D, for example, T7901, T7903, T8201, T8202, T8402, and T8506. These strains are accessible from Northeastern University's Ocean Genome Legacy Center of New England Biolabs.

In an aspect, tartrolon D is produced by *T. turnerae* strain T7901 and subsequently purified. In one embodiment, sequenced strain *T. turnerae* T7901 was isolated by John Waterbury, Woods Hole Oceanographic Institution from a specimen of the shipworm *Bankia gouldi* collected from the Newport River Estuary, Beaufort N.C. in 1979. This strain, and 53 similar strains of *T. turnerae* isolated from a variety of shipworm species collected by Waterbury et al. between 1979 and 1986, have been deposited to Ocean Genome Resource project (OGR accession number 100002), a public biorepository operated by Northeastern University's Ocean Genome Legacy Center of New England Biolabs, located at 430 Nahant Rd, Nahant, Mass., USA 01908. The sequenced strain has also been deposited at the American Type Culture Collection in Manassas, Va., USA (accession number 39867).

Tartrolon D is not commercially available. Examples of media and protocols that can be used to grow *T. turnerae* strains that produce tartrolon D include but are not limited to:

Media: Seawater obtained from Revere Beach, Mass., supplemented with 0.5% sucrose (or other appropriate carbon source such as, but not limited to xylose or cellulose), 0.25% $NH_4Cl$, 20 mM HEPES and 1.5% minerals and metals solution (7.5 mM $K_2HPO_4$, 7 mM $Na_2CO_3$, 3.5 mM boric acid, 1 mM citric acid, 0.75 mM Ferric ammonium citrate, 0.7 mM $MnCl_2$, 0.7 mM $Na_2MoO4$, 80 µM EDTA, 70 µM $ZnSO_4$, 21 µM $CuSO_4$, 14 µM $Na_2MoO_4$, 14 µM $Co(NO_3)$). This solution is hereafter referred to as "complete SBM".

Protocol: Bacteria from frozen stabilates are thawed and grown in 3 mls of SBM with 1% xylose as a carbon source. The bacteria are grown at 35° C. and at 35 rpm (standard growth conditions maintained throughout) for 48 hours or until there is significant growth as determined by the cloudiness of the media. These cultures are streaked out onto agar plates made with SBM containing 1% xylose and 1% Bacto agar. When individual bacterial colonies can be seen, these are picked and each colony grown for 24-72 hours in 3 mls of SBM plus 1% xylose until growth can be observed (usually stringy clumps). The 3 mls of culture are transferred into 20 mls of SBM plus 1% xylose in a 200 ml Erlenmeyer flask and grown for 24 to 48 hours until growth in clumpy strings is observed. The 20 mls of culture is seeded into 180 mls of SBM-1% xylose in a 2.5 liter, low form culture flask and incubated for 24-48 hours until stringy clumps of growth are evident. The culture is transferred to 50 ml centrifuge tubes and the bacterial pellet is obtained by centrifugation at 3500 g for 30 minutes. The supernatant is discarded and the pellets stored at −80° C. until extraction.

*T. turnerae* naturally makes the polyketide metabolite tartrolon D. Its boronated form is tartrolon E (FIGS. 1C and 1D). Boron is ubiquitous: it is abundant in the sea, and there are significant amounts of boron in fetal calf serum, which is 15% of the media used to grow the cells and parasites in experiments described here. Addition of extra boron to the cultures did not affect observed anti-parasitic activity. Tartrolon A was shown to pick up boron (forming tartrolon B) by simply being stored in borosilicate glass containers (Irschik H et al. (1995) *J. Antibiot* (Tokyo) 48(1):26-30), suggesting that tartrolon D should also pick up boron from the solution or glass container easily and become tartrolon E—the two most likely co-exist in an equilibrium. See also, Mulzer J et al., (2004) *J Org. Chem.* 69:891-898. Tartrolon D or E, individually (including all stereoisomers), or both together, appeared to be active against tested pathogens. Accordingly, the principle of the present invention, which is predicated on the effectiveness of either tartrolon D or E individually, or the two in combination, has been proven valid as addition of extra boron to *T. turnerae* cultures did not affect the observed anti-parasitic activities. It is further noted that the invention includes the three stereoisomers/epimers/anomers, of Tartrolon D and the three stereoisomers/epimers/anomers of Tartrolon E, based on the alpha and beta orientations (i.e., "up or down") of the two hydroxyl groups alpha to the two carboxyl groups (FIGS. 1C and 1D). These stereoisomers/epimers/anomers transform into one another and appear to have the same or similar activity against apicomplexan species.

For purpose of disclosure, where either tartrolon D or E is described as one of the starting materials and in solution, it should be assumed that during the time period of the bio-significant interactions under study, at least some amount of the starting materials have converted to tartrolon E or D, respectively, unless it is expressly specified otherwise (e.g., in a boron-free environment). Therefore, any data presented under such conditions should be viewed as supporting the materials under study included both tartrolons D and E even if only one is mentioned.

In an embodiment according to the present invention, tartrolon D is biosynthesized as previously described in Elshahawi, S et al. (2013) *PNAS USA* 110(4):E295-E304. In an alternate embodiment, tartrolon D/E is produced using recombinant genetic technologies. For example, a host organism can be cloned to recombinantly express forms of genes coding for tartrolon production, such as a plasmid that has incorporated part or all of region 2 of the trt cluster (Cluster 2) from the genome of *T. turnerae*, preferably the strain T7901, which encodes the enzymes that produce the polyketide tartrolon D, and hence its boronated derivative, tartrolon E with any source of boron. The sequences of the cluster 2 genes that produce Tartrolon D/E are found in the NCBI data base under the gene symbols: TERTU 2188, TERTU 2189, TERTU 2190, TERTU 2191, TERTU 2193, TERTU 2194, TERTU 2195, TERTU 2198, TERT 2199, TERTU 2200, TERTU 2202, TERTU 2203, TERTU 2204, TERTU 2205, TERTU 2206, TERTU 2207, TERTU 2208, TERTU 2209, TERTU 2211, TERTU 2212. The functions of each gene have been described in Elshahawi et al 2013. Alternatively, *T. turnerae* strains may be genetically engineered to overexpress the genes involved in tartrolon production by methods including, but not limited to, modification of expression of regulatory genes, genes encoding synthesis of signaling molecules, improvement of precursor availability, overexpression, inactivation and engineering of structural genes overexpression of resistance genes and export genes and ribosome engineering. Host organisms suitable for the cloning include bacteria such as, but not limited to, *Escherichia coli, Streptomyces* or other Actinomycetes or fungi such as, but not limited to *Aspergillus, Fusarium* or *Saccharomyces*.

After tartrolon D has been produced, boric acid or another source of boron is then, should it be needed to practice the invention, added to transform tartrolon D to tartrolon E, or a mixture thereof. To be clear, in one aspect, the invention can be practiced with only tartrolon D as the active ingredient, but in another aspect, the invention is practiced with only tartrolon E as the active ingredient. Yet in a third aspect, the invention is practiced with a mixture of tartrolons D and E. In order to practice the latter two aspects, in one feature, the growth medium used for biosynthesizing tartrolon D generally provides a source of boron sufficient to enable the production of tartrolon E. Generally, the amount of boron in seawater ranges from about 0.5 up to about 4 mg/kg, and is generally at least about 0.426 mM. However, any range provided that can incorporate boron within the parameters of the present invention is equally suitable for practicing the principle of the invention. And while the seawater source providing the aforementioned range is beneficial, it is to also be understood that any source of boron can also be utilized for the aforementioned purposes. An exemplary range when using such an alternative boron source includes at least about 0.01 mg/kg to be incorporated into a given structure disclosed herein to enable a tartrolon E configuration, as described in the present application.

For example *T. turnerae* is readily propagated in a broth consisting predominantly of "seawater" (seawater collected from the ocean at Revere Beach, Mass., USA) and a carbon source. Suitable carbon sources include but are not limited to: sucrose, xylose, glucose, galactose, and the like and powdered cellulose such as Sigmacel (Sigma-Aldrich cat #S3504) or Avicel (Sigma-Aldrich cat #11365) and carboxymethyl cellulose. All these carbon sources are commercially available. One or more than one of any of these may be used as a carbon source.

Practical and effective amounts of the tartrolons described herein can be produced and purified from one or both of the culture supernatant and the cell lysate. Exemplary isolation/purification protocols are described in the Examples section below.

Alternatively, the tartrolons that are used as described herein are obtained from another bacterial species, e.g., from *Streptomyces* sp. MDG-04-17-069. The microbial producer *Streptomyces* sp. MDG-04-17-069 (from a marine sediment collected near the east coast of Madagascar, Genbank accession #GU211218) was grown on 172B modified agar medium 12 plates supplemented with nalidixic acid (1%). Plates were incubated at 28° C. for 30 days. The seed culture from a single colony was grown first in 100 mL Erlenmeyer flasks containing 20 mL of seed medium and then in 250 mL Erlenmeyer flasks with 50 mL of the same medium. The medium for growth of the bacteria is: dextrose (0.1%), soluble starch (2.4%), soy peptone (0.3%), yeast extract (0.5%), Tryptone (0.5%), soya flour (0.5%), NaCl (0.54%), KCl (0.02%), MgCl (0.24%), $Na_2SO_4$ (0.75%), and $CaCO_3$ (0.4%) in tap water and cultured at 28° C. on orbital shakers for 72 h. For production, 12.5 mL of the seed medium was transferred into 2 L Erlenmeyer flasks containing 250 mL of fermentation medium containing yeast extract (0.5%), soy peptone (0.1%), dextrose (0.5%), soya flour (0.3%), Glucidex (Roquette, France) (2%), NaCl (0.53%), KCl (0.02%), $MgCl_2.6H_2O$ (0.24%), $Na_2SO_4$ (0.75%), $MnSO_4.4H_2O$ (0.00076%), $CoCl_2.6H_2O$ (0.0001%), $K_2HPO_4$ (0.05%), and $CaCO_3$ (0.4%). The culture was grown at 28° C. using an orbital shaker (5 cm eccentricity, 220 rpm) for 5 days. TrtD was obtained by reversed phase C-18 column chromatography and repeated preparative and semi-preparative reversed-phase HPLC of EtOAc extracts of the supernatant of culture broths of the actinomycete. (see Perez et al. (2009) *J Nat Prod,* 72(12): 2192-2194).

Alternatively, the tartrolons that are used as described herein may be chemically synthesized. An exemplary chemical synthesis of these compounds is described in Kim et al. (2006) *Org Lett,* 8(23): 5219-5222, using a silicon-tethered ring-closing metathesis strategy.

Compositions

The compounds described herein are generally delivered (administered) as active ingredients in a pharmaceutical composition. Such pharmaceutical compositions generally comprise at least one of the compounds disclosed herein, i.e. one or more than one (a plurality) of the compounds of the invention (e.g. 2 or more) may be included in a single formulation. Accordingly, the present invention encompasses such formulations/compositions. The compositions generally include one or more substantially purified compounds as described herein, and a pharmacologically suitable (physiologically compatible) carrier, which may be aqueous or oil-based. In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the active ingredients are mixed with excipients which are pharmaceutically acceptable and compatible with the active ingredients, e.g. pharmaceutically acceptable salts. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of compound in the formulations varies, but is generally from about 1-99%. Still other suitable formulations for use in the present invention are found, for example in *Remington's Pharmaceutical Sciences,* 22nd ed. (2012; eds. Allen, Adejarem Desselle and Felton). In some aspects, the compositions are food, animal feed, or food supplements. The tartrolons may also be administered as prodrugs, i.e. as a biologically inactive compound that can be metabolized in the body to produce the drug. The pharmaceutical composition may be formulated to achieve controlled release for the active ingredients.

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," *J. Pharm. Sci.,* 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

Accordingly, the invention provides a pharmaceutical composition comprising tartrolon D, E or both and a pharmaceutically acceptable excipient, carrier, or diluent, optionally with a second or more anti-parasitic agent (e.g., to prevent development of drug resistance). Non-limiting examples of additional anti-parasitic agents that can be used in combination with compound(s) of the invention, e.g., in the same or separate pharmaceutical composition, include and are not limited to: nitazoxinide, atovaquone and proguanil (individually or in combination), artemisinin and piperaquine (individually or in combination), chloroquine, mefloquine, doxycycline, amodiaquine, lumefantrine, sulfadoxine/pyrimethamine, quinine and clindamycin (individually or in combination), primaquine, and tafenoquine.

In a particular embodiment, the invention provides an animal feed comprising tartrolon D, E or both, in a concentration that is effective to inhibit a disease that is caused by an apicomplexan pathogen. The feed can be intended for domesticated farm animals such as ruminant, poultry, camelids, pig, fish or wild animals such as sea mammals. Common examples of animal feed include and are not limited to: hay, silage, pelleted feeds, straw, grains (e.g., oat, wheat, barley, rice, maize and soy bean), and legumes. In a further embodiment, the invention provides a food supplement intended for human consumption that contains sufficient concentration or amount of tartrolon D or E or both.

Administration

In an embodiment of the present invention, a therapeutically effective amount of the compound(s) of the invention is administered to a subject, e.g., a person or an animal, to treat or prevent an infection caused by an apicomplexan parasite, e.g., *Cryptosporidium parvum, Toxoplasma gondii,*

*Babesia bovis, Plasmodium, Cyclospora cayetanensis, Isospora belli Sarcocystis Besnoitia, Hamondia, Neospora,* or *Theileria*. The corresponding disease thus treated by the compound(s) of the invention may include cryptosporidiosis, toxoplasmosis, babesiosis, malaria, cyclosporiasis, isosporiasis, sarcosporidosis, besnoitiosis, hammondiosis, neosporosis, and theileriosis (also known as East Coast fever). For administration, the compound(s) of the invention may be formulated into a pharmaceutical composition, by mixing a therapeutically effective amount of the compound(s) of the invention with a pharmaceutically acceptable excipient, carrier, or diluent.

In an embodiment, a therapeutically effective amount of the compound(s) of the invention is combined with a second or more anti-parasitic agent to treat or prevent the infection by an apicomplexan parasite described herein.

Administration of the composition of the invention may be by any means known in the art, including: orally, intravenously, subcutaneously, via inhalation, intraarterially, intramuscularly, intracardially, intraventricularly, parenteral, intrathecally, and intraperitoneally. Administration may be systemic, e.g. intravenously, or localized. In other words, the compositions of the invention may be administered in vivo by any suitable route including but not limited to: inoculation or injection (e.g. intravenous, intraperitoneal, intramuscular, subcutaneous, intra-aural, intraarticular, and the like), topical application (e.g. on areas such as eyes, skin, in ears or on sites of infection) and by absorption through epithelial or mucocutaneous linings (e.g., nasal, oral, vaginal, rectal, gastrointestinal mucosa, and the like). In some embodiments, the mode of administration is oral, inhalation or by injection.

Those of skill in the art will recognize that the exact dose that is administered to a subject will vary according to several factors, e.g. the specific dose level for any particular animal (such as a human) will depend upon a variety of factors including the activity of the specific compound employed, the age, body weight, general health, gender, diet, time of administration, route of administration and rate of excretion, drug combination and the severity of the particular disease undergoing therapy, etc. Generally, the tartrolons are administered to a host at a total dose (including all tartrolons and/or isomers administered) of from about 0.01 up to about to 5000 mg/kg of body weight, e.g. from about 0.5 to about 5000 mg/kg, such as about 0.5, 1.0, 1.5, 2.0, 2.5, 3.0, 3.5, 4.0, 4.5, 5.0, 40, 50, 500, 1000, 5000. In some aspects, the dose is about 2 mg/kg (e.g., for treatment of infections caused by *Cryptosporidium parvum*, or *Plasmodium* sp.). Dosing may be carried out according to any suitable schedule, e.g. daily, or 2-4 times daily, etc. for a suitable period of time, e.g. until the danger of infection is past, or until one or more (or all) symptoms of prior infection dissipate or disappear. For example, administration may be performed for about 3-5 days, or for about 7-10 days, etc. If the tartrolons are administered as a food supplement, such as in animal feed, administration may be ongoing and may occur each time the animal feeds. In fact, administration may be ongoing for any form of the compositions in that in some aspects, administration occurs repetitively, e.g. once per week, once per month, etc. on an ongoing basis, particularly if the subject resides in an area where the parasite of interest and/or its vector is endemic. Dosage amount and interval can be adjusted individually to provide plasma levels of the active moiety that are sufficient to maintain protozoa cell killing and/or growth inhibitory effects. Usual dosages for systemic administration range from about 0.001 to 5000 mg/day, e.g., about 1-500 mg/day, or about 10-200 mg/day, or even 100-200 mg/day.

The host to whom the compositions are administered is generally a mammal and in some aspects is a human, e.g. when the parasite is, for example, *Cryptosporidium* sp. and the disease that is prevented or treated is cryptosporidiosis, *Toxoplasma gondii* and the disease is toxoplasmosis; or the parasite is a *Plasmodium* and the disease is malaria, etc. In other aspects, the host is a non-human mammal (such as a bovine), the parasite is *Cryptosporidium* and the diseases is cryptosporidiosis, *Theileria parva* and the disease is East Coast Fever, or the host is an equine, bovine, or sea mammal and the parasite is *Sarcocystis* and the disease is sarcocystosis or equine protozoal myeloencephalitis (EPM), or the host is a ruminant or pig where the parasite is *Eimeria* or *Isospora* and the disease is coccidiosis, or the host is a ruminant, dog or sea mammal where the parasite is *Neospora* and the disease is neosporiasis, or the host is a bovine or rabbit and the parasite is *Besnoitia* and the disease is besnoitiosis, or the host is a dog where the parasite is *Hammondia* and the disease is hammondiasis. In some aspects, the tartrolons are provided as a food or food supplement i.e. as a comestible substance. The food supplement may be formulated for any type of host that is susceptible to infection by the Apicomplexan parasites described herein.

In addition, the compositions may be administered or provided in conjunction with other treatment modalities such as antibiotics, anti-protozoan agents, adjuvants and other substances that boost the host's immune system, various chemotherapeutic agents, and the like. In some aspects, the one or more tartrolons are administered or provided with a second anti-parasitic agent (e.g., as part of a combinational regimen), examples of which include but are not limited to: nitazoxinide, atovaquone, proguanil, artemisinin, piperaquine, chloroquine, mefloquine, doxycycline, amodiaquine, lumefantrine, sulfadoxine/pyrimethamine, quinine and clindamycin, primaquine, and tafenoquine. Accordingly, the disclosure also provides compositions comprising one or more (at least one) tartrolon or isomer thereof as described herein and at least one additional (i.e. a second) anti-parasitic agent. Such compositions may be medicaments provided for administration as described above, or food supplements, also as described above.

As described herein, the tartrolons of the invention are administered or provided to a host or potential host of a parasite described herein. If a host of interest is not already infected but is at risk of infection (e.g. lives in or travels to a location where infection by at least one parasite of interest is possible or likely (probable), e.g. where contact with a vector which carries an infectious life cycle stage of the parasite e.g. by biting or ingestion) is possible or likely, the compositions described herein are administered prior to infection (prophylactically) to prevent or ward off at least one symptom of infection. Alternatively, a host of interest may be known to be already infected by one or more of the parasites described herein. In the latter case, the compositions are administered in order to treat and, in some aspects, to cure, the disease. While a desired outcome is complete prevention or eradication of all symptoms of infection, those of skill in the art will recognize that much benefit can accrue even if some symptoms are only lessened, or if the duration of the infection is shortened, or if the ability of a vector to be infected is decreased or curtailed, etc.

In various embodiments of the invention, the compounds of the invention, based on their ability to inhibit the growth of apicomplexan pathogens at nanomolar (nM) or picomolar (pM) concentrations, are used as a cleanser, suppressant or disinfectant to clean, suppress, inhibit, kill or disinfect a substantial amount (more than 20%, 30%, or 40%), preferably more than 50%, more preferably more than 60%, 70%, 80%, 90%, or 95% apicomplexan pathogens. In an embodiment, a composition having at least one compound of the invention is used to disinfect at least one of selected apicomplexan pathogens that include but are not limited to: *Cryptosporidium parvum, Toxoplasma gondii, Babesia bovis, Plasmodium, Cyclospora cayetanensis, Isospora belli Sarcocystis, Hammondia, Besnoitia, Neospora* or *Theileria* in an area or a subject. The disinfectant can be made in the form of a solution, gel, cream, oil, powder, solid tablet/bar or mixtures of any of the above, in read-to-use concentrations or concentrated forms. The compound(s) of the invention can also be made as a supplement to human food or animal feed to neutralize and remove the above parasites from a subject.

Targeted Parasites

The parasites that are killed or in which growth and/or reproduction is inhibited are Apicomplexan parasites. Examples of genera which can be targeted by the compositions and methods disclosed herein include but are not limited to: *Cryptosporidium, Babesia, Cyclospora, Isospora, Eimeria, Plasmodium, Sarcocystis, Theileria, Toxoplasma, Besnoitia, Hammondia,* and *Neospora*. Exemplary *Cryptosporidium* species include but are not limited to: *Cryptosporidium parvum, Cryptosporidium hominis, Cryptosporidium andersoni,* and *Cryptosporidium fells*. Exemplary *Babesia* species include but are not limited to: *Babesia microti, Babesia duncani, Babesia divergens* and *Babesia bovis*. Exemplary *Cyclospora* species include but are not limited to: *Cyclospora cayetanensis*. Exemplary *Isospora* species include but are not limited to: *Isospora belli, Isospora canis, Isospora fells, Isospora suis,* and *Isospora hominis*. Exemplary *Plasmodium* species include but are not limited to: *Plasmodium falciparum, Plasmodium vivax, Plasmodium ovale* and *Plasmodium malariae*. Exemplary *Theileria* species include but are not limited to: *Theileria annulata, Theileria parva* and *Theileria equi*. Exemplary *Toxoplasma* species include but are not limited to: *Toxoplasma gondii*. Exemplary *Sarcocystis* species include but are not limited to: *Sarcocystis neurona, Sarcocystis fells, Sarcocystis cervi,* and *Sarcocystis cruzi*. Exemplary *Eimeria* species include but are not limited to: *Eimeria bovis, Eimeria tenella,* and *Eimeria zuernii*. Exemplary *Besnoitia* species include but are not limited to: *B. besnoiti* and *B. oryctofelisi*. Exemplary *Hammondia* species include but are not limited to: *H. hammondi* and *H. heydorni*. Exemplary *Neospora* species include but are not limited to: *N. caninum* and *N. hughesi*.

Disease symptoms which are prevented, prophylactically treated, eliminated or lessened by the methods and compositions disclosed herein include but are not limited to: fever, diarrhea, gas, upset stomach, greasy stools, dehydration, stomach cramps, stomach pain, nausea, vomiting, weight loss, lethargy, malaise, predisposition to other diseases or death. However, those of skill in the art will recognize that an infection can occur with no or very few overt or acute symptoms and yet be detrimental to the overall health of the subject or other subjects. For example, there may be few symptoms in a young, otherwise healthy adult but that adult can serve as a carrier of the parasite, providing a host by which a vector contracts an infection which is then transmitted to a more susceptible host, such as an elderly or very young person, an immunocompromised subject (e.g. a subject undergoing cancer treatment), and the like.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

To aid the reader in understanding the possible various embodiments of the present invention, the following examples provides reference when considering the embodiments herein, which is intended to be illustrative only, but not limiting thereof.

EXAMPLES

Example 1: In Vitro Activity of *Teredinibacter turnerae* T7901 in Culture Supernatants and Cell Pellets Against *Toxoplasma gondii*

To determine if *T. turnerae* produced compounds that could inhibit the growth of the obligate intracellular apicomplexan pathogens, a target parasite, *Toxoplasma gondii*, was grown in medium containing dilutions of *T. turnerae* culture supernatant or dilutions of *T. turnerae* cell pellet lysates. The *T. turnerae* strain, T7901, was tested for activity against *Toxoplasma gondii*.

*T. turnerae* strains were first grown in Shipworm Bacteria medium (SBM) prepared as previously described in Waterbury J B et al. (1983) *Science* 221(4618):1401-1403, and supplemented with ingredients such as 0.5% sucrose and 0.25% NH$_4$Cl into complete SBM as described above. Bacterial cultures were prepared by seeding frozen stabilates of the *T. turnerae* strains into 3 mls of the complete SBM. After 3 days of growth, they were transferred into 100 ml flasks each containing 15-20 mls of the complete SBM. These cultures were grown for 9 days at 30° C. with shaking at approximately 35 rpm. The cultures were centrifuged for 30 minutes at 4000×g and the supernatant and the pellets collected separately. The pellet was lysed in Bugbuster (EMD Millipore) following manufacturer's directions and the soluble fractions sterilized by passage through a Spin-X, 0.2 µm filter (Corning Costar).

Alternately, the bacteria were grown with either xylose or cellulose as the carbon source (replacing sucrose), at 35° C., for 1-4 days, which improved the viability of the bacteria resulting in increased anti-parasitic activity of the cultures. Bacteria grown at 35° C. grew more rapidly and consistently than at 30° C. Several carbon sources were tested and bacteria grew well in sucrose, xylose and Sigmacel cellulose. The anti-parasitic activity of bacteria grown in each carbon source was compared by collecting and lysing the bacterial pellet and testing the lysate for anti-toxoplasma activities. The potency of the bacterial lysates was evaluated by adding dilutions of the bacterial lysates to human foreskin fibroblast (HFF) cells that had been infected with *Toxoplasma gondii* for 24 hours. Then, 48 hours after the addition of the bacterial lysate dilutions, the efficacy of the dilutions was determined by microscopic evaluation of parasitemia. This way, it was determined that xylose was the preferred carbon source for tartrolon D production, and 24 to 48 hours of growth in the 2.5-liter flasks was the optimal time for collection. In a comparison of cultures grown for 4 days versus 1 day in the 2.5-liter flasks, four times more tartrolon D was recovered after 24 hours than was recovered after 4 days.

Monolayer protection assays were performed as follows: human foreskin fibroblast (HFF) cells were seeded into the wells of a 96-well plate (approximately 2×10$^5$ cells per well) and allowed to reach confluence (about 24 hours post seeding). Once confluent, the cells were infected with *T. gondii* (5×10$^4$/well). Supernatants and pellet lysates of *T. turnerae* T7901 were added either at the same time as the parasites or were added 24 hours post-infection. The plates were then incubated (37° C., 5% CO$_2$) until parasites in the untreated wells had lysed all the HFFs. To the monolayers were then added trypan blue. Intact monolayers, protected from parasite proliferation, remained adhered to the plate and stained blue, indicating anti-parasitic inhibition by the supernatants and pellet lysates.

The results showed that both culture supernatant and cell pellet lysates from T7901: (1) prevented infection of the host cells by the parasites, and (2) irreversibly blocked growth of intracellular stages of the parasites. After 24 hours in the presence of the bacterial supernatant or lysate, parasite vacuoles and parasite nuclei remained intact but there were no morphologically intact parasites within the vacuole (internal data). Effective dilutions of culture supernatant ranged from 1:100 to 1:500.

Example 2: Identification of Tartrolon D/E as the Active Compounds in T7901 Cell Lysates Approximately 1 liter of T7901 culture was grown under conditions that encouraged the formation of biofilms. To induce biofilm formation, bacteria were grown in test tubes in 3 mls of the complete SBM for 3 days, then the 3 ml bacterial culture was transferred to a larger flask that already contains 27 mls of complete SBM using sucrose as a carbon source. After 3-5 days of growth, this 30 ml culture was transferred to a 1 liter wide bottom flask already containing 170 mls of the complete SBM, bringing the total volume to 200 ml. The culture was allowed to grow for another 5-7 days. All cultures were grown at 30° C. while shaken at 35 rpm in experiments described here in the specification unless otherwise noted. The 200 ml culture was then transferred to multiple 50 ml tubes and centrifuged at 6000×g to separate the pellet and supernatant. Culture supernatant and cell pellets were collected and underwent bioassay-guided fractionation.

After cells were separated from the media through centrifugation, 100 ml media was extracted three times with ethyl acetate (75 ml). The ethyl acetate fraction was dried under vacuum to yield an extract (25 mg). This was dissolved in methanol (2 ml), which was loaded onto end-capped C18 resin (2 g). The loaded resin was dried under vacuum and loaded onto a column containing additional C18 resin (5 g). The column was washed with water (50 ml), then fractions were eluted using a methanol/water step gradient (20%, 40%, 60%, 70%, 80%, 90% and 100% methanol, respectively; 100 mL each), to provide fractions Fr1 to Fr7, respectively, which were then dried under vacuum. The seven fractions were re-suspended in DMSO to 1 mg/ml and further diluted in cell culture medium for bioassay testing that included monolayer protection assays and immunofluorescence assays.

For the monolayer protection assay, human foreskin fibroblast (HFF) cells were seeded into the wells of a 96-well plate (approximately 2×10$^5$ cells per well) and allowed to reach confluence (about 24 hours post seeding). Once confluent, the cells were infected with one of the Apicomplexan parasites, *T. gondii* (5×10$^4$/well). Twenty-four hours after the infection, the infected cells were treated with various dilutions of the HPLC fractions Fr1 to Fr7, namely, twofold dilutions from 100 µg/ml to 200 ng/ml. The plates were then incubated (37° C., 5% CO$_2$) until parasites in the untreated wells had lysed all the HFF cells (approximately 72 hours post treatment). Intact monolayers, protected from parasite proliferation, stained blue, indicating anti-parasitic inhibition by the fraction.

Figure 2:
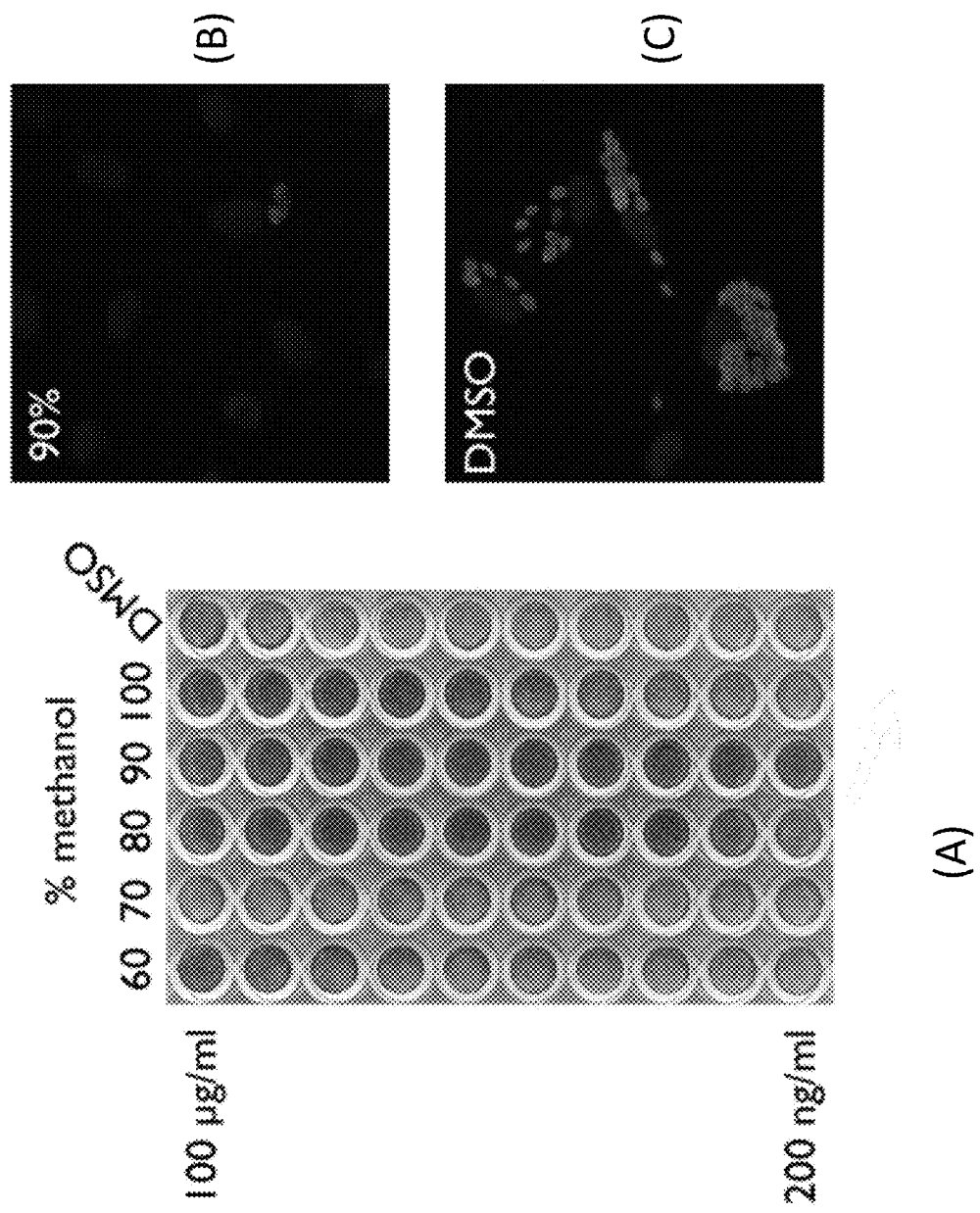
FIGS. 2A-2C show results of screening HPLC fractions against intracellular *T. gondii*: (2A) results of a host cell monolayer protection assay (five of the seven fractions are shown); (2B) and (2C): results of immunofluorescence assay where (2B) shows result using the fraction extracted with 90% methanol and (2C) shows result with the DMSO control.

FIG. 2A shows the results for five of the seven fractions that were tested. As can be seen, Fractions 5-7, which were eluted with 80%, 90% and 100% methanol, respectively, were identified as the most active fractions, since most of the wells stained blue in the three associated columns, indicating that the HFF cells were protected from infection. The column for Fraction 6 (eluted with 90% methanol) in particular, showed staining at all concentrations tested.

FIGS. 2B and 2C show results for experiments that were conducted as for FIG. 2A, except that 24 hours after addition of the fractions, the infected HFF cells were processed for immunofluorescence assays. Briefly, infected and treated HFF cells that had been grown on coverslips in 6-well plates were fixed with methanol and parasites were detected using antibody to the SAG1 *T. gondii* surface antigen that was then detected with a red-fluorescence tagged secondary antibody. Host nuclei were stained with blue fluorescent marker DAPI (4',6-diamidino-2-phenylindole). Host nuclei were clearly visible (blue) in all cell populations in both FIGS. 2B and 2C. Consistent with the trypan blue results, extensive red fluorescence was visible in cells treated with the control (DMSO) in FIG. 2C, meaning these cells were highly infected with the parasites. In contrast, very little red fluorescence was observed in cells treated with, e.g. Fraction 6, the fraction eluted with 90% methanol (FIG. 2B).

The results here show that Fractions 5-7 (eluted with 80%, 90% and 100% methanol, respectively) were the most pronounced fractions in terms of their anti-parasitic effect. As fractions 5-7 were highly enriched in tartrolon D (see Example 3), it was hypothesized that this compound was the source of the observed anti-parasitic activity.

Example 3: Isolation and Characterization of the Anti-Parasitic Agent

Figure 3A:
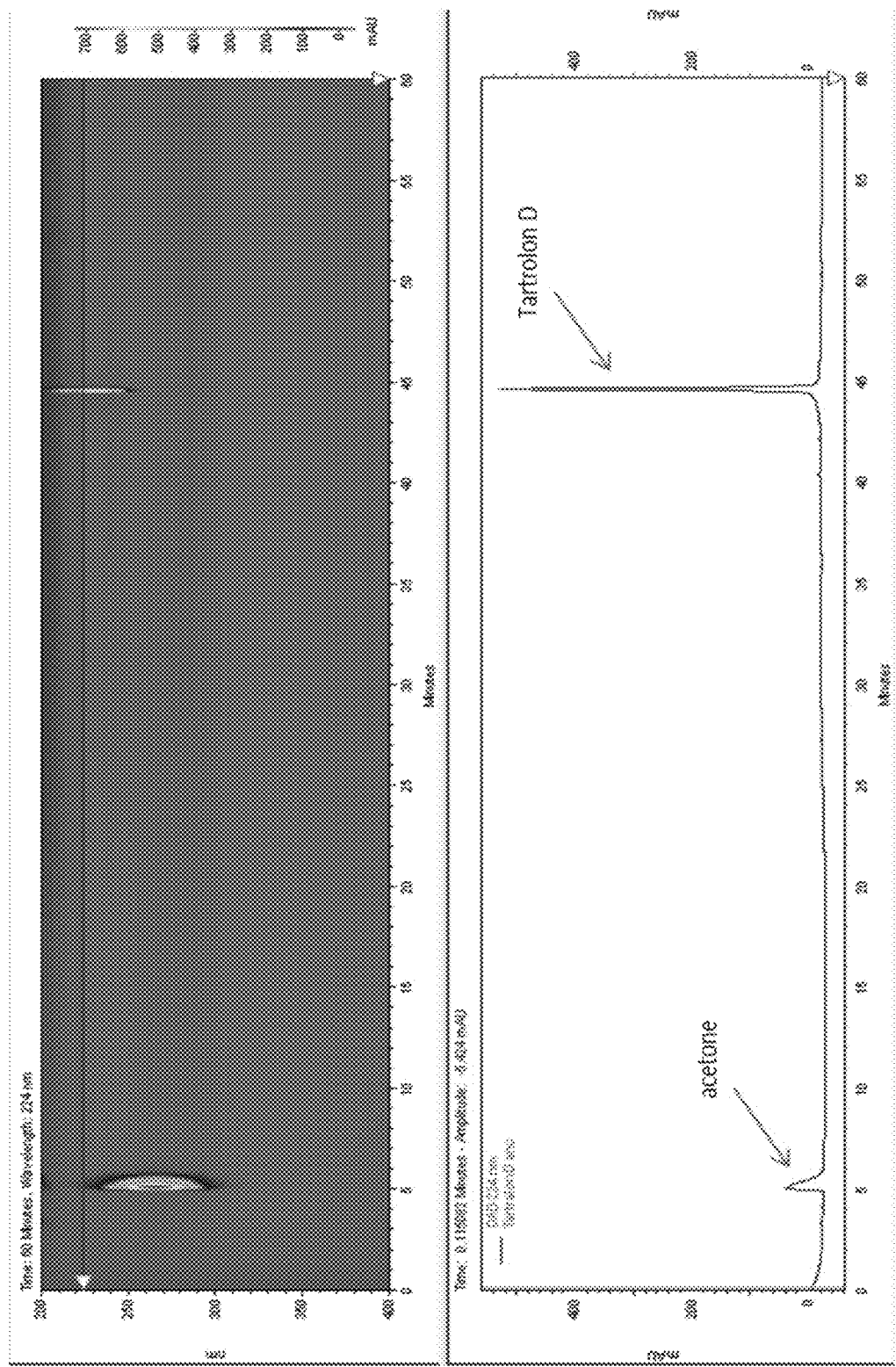
FIGS. 3A-3C show analysis of tartrolon D.
Figure 3B:
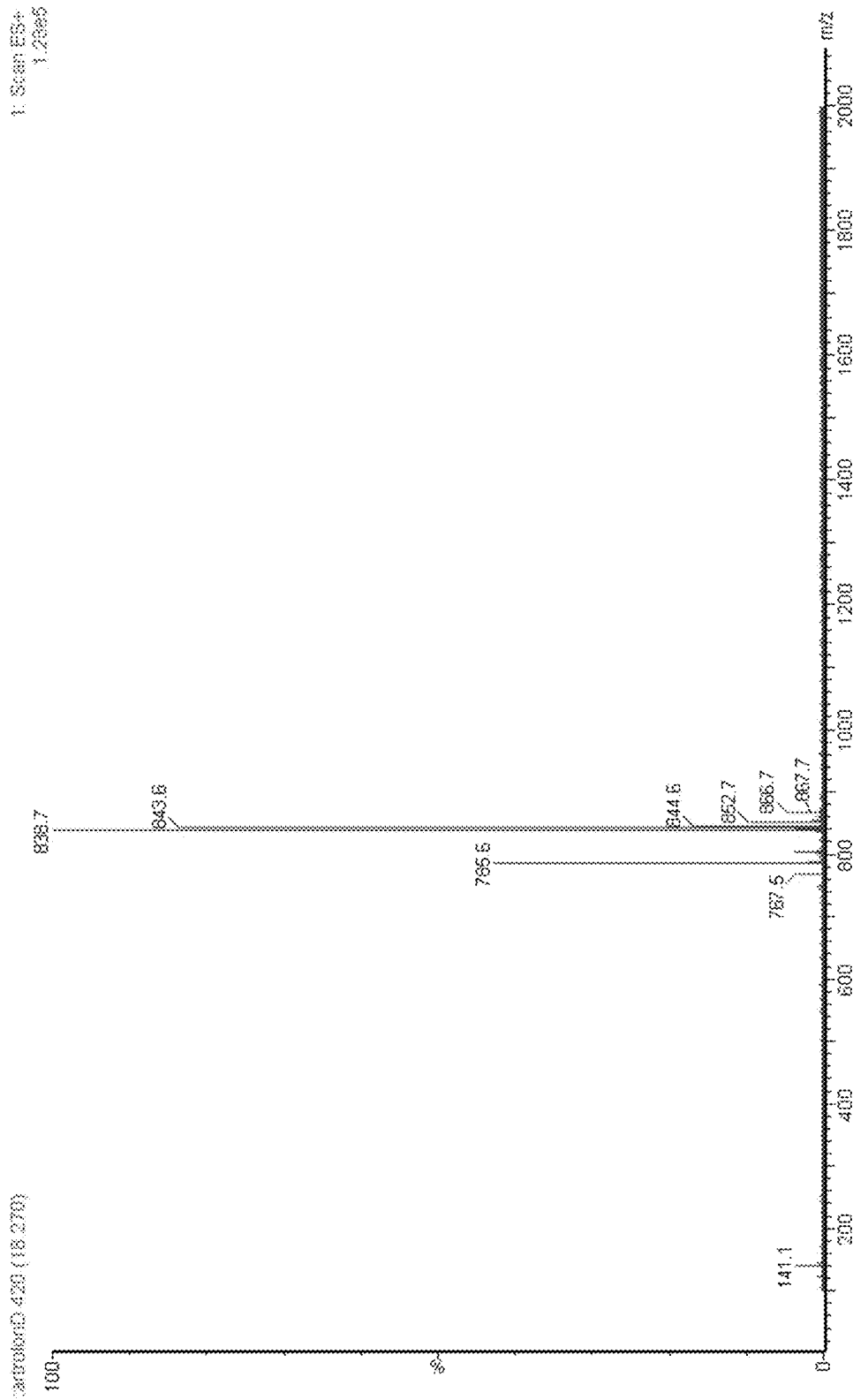
Figure 3C:
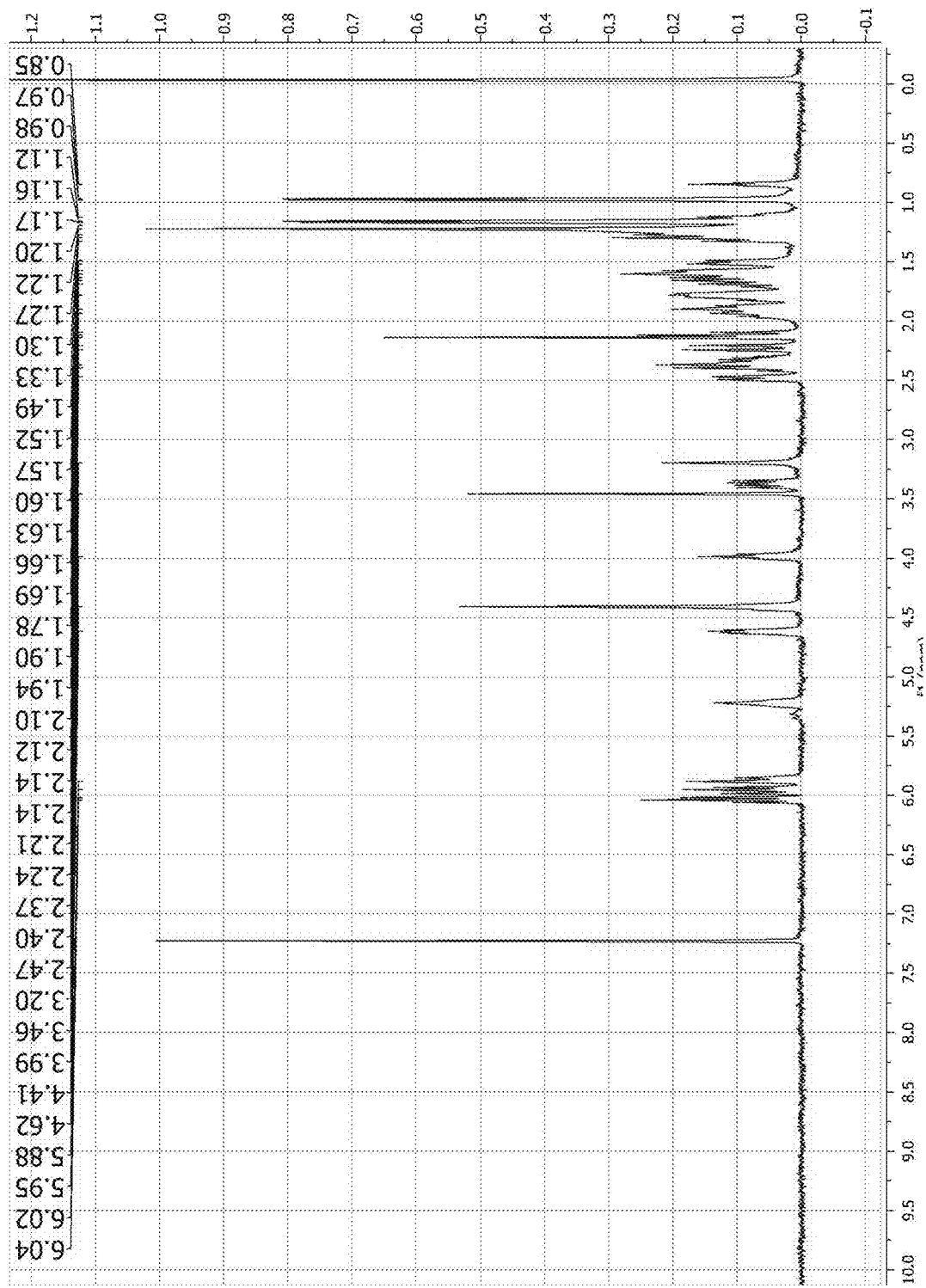

It was hypothesized that Tartrolon (see below) was the source of the anti-parasitic activity. To test this hypothesis, a cell pellet from the T7901 culture was extracted three times with acetone (100 mL). The solution was dried under vacuum to yield an extract (70 mg), which was dissolved in methanol (2 mL) and flushed through a cartridge containing end-capped C18 resin. The flow-through was purified by HPLC using 85% acetonitrile in water to obtain tartrolon D (1.7 mg). This compound was previously purified from the same bacterial strain, and its identity was confirmed by comparing data (HLPC chromatogram, mass spectrometry, and NMR, as shown in FIGS. 3A-3C, respectively) with previously reported data on tartrolon D (Elshahawi, et al., (2013), supra), namely: LC-ESIMS m/z 843 [M+Na]$^+$, 866 [M+2Na]$^+$ and UV λmax 231 nm (MeOH)).

Specifically in FIG. 3A, for instance, a Phenomenex Onyx Monolithic semiprep C18 column (100×10 mm) was used for HPLC, as conducted on a Hitachi Elite Lachrom System equipped with a Diode Array L-2455 detector. LC/ESI-MS was performed using a Micromass Quattro-II (Waters) instrument on an analytical Agilent Eclipse XDB-C18 column (4.6×150 mm, 5 µm) with a linear gradient of 1%-99% B over 20 minutes, where the mobile phase consisted of solvent A (H$_2$O with 0.05% formic acid) and solvent B (ACN).

Example 4: Preparation and Characterization of Tartrolon D

Growth of *Teredinibacter turnerae* with xylose as a carbon source at 35° C. followed by isolation of tartrolon D using a different purification protocol yielded a different preparation of tartrolon D (referred to as "tartrolon D$_2$" hereinafter) separate from the one obtained (referred to as "tartrolon D$_1$" for distinction) in Example 3.

The cultivation protocol for Tartrolon D$_2$ was as follows: Bacteria from frozen stabilates were thawed and grown in 3 mls of SBM with 1% xylose as a carbon source. The bacteria were grown at 35° C. and at 35 rpm (standard growth conditions maintained throughout) for 48 hours or until there was significant growth as determined by the cloudiness of the media. These cultures were streaked out onto agar plates made with SBM containing 1% xylose and 1% Bacto agar. When individual bacterial colonies were seen, these were picked and each colony grown for 24-72 hours in 3 mls of SBM plus 1% xylose until growth was observed (usually stringy clumps). The 3 mls of culture were transferred into 20 mls of SBM plus 1% xylose in a 200 ml Erlenmeyer flask and grown for 24 to 48 hours until growth in clumpy strings was observed. The 20 mls of culture was seeded into 180 mls of SBM-1% xylose in a 2.5 liter, low form culture flask and incubated for 24-48 hours until stringy clumps of growth were evident. The culture was transferred to 50 ml centrifuge tubes and the bacterial pellet was obtained by centrifugation at 3500 g for 30 minutes. The supernatant was discarded and the pellets stored at −80° C. until extraction.

The purification scheme for Tartrolon D$_2$ from the bacterial pellets was as follows: a cell pellet resulting from 1.2 L of T7901 culture was extracted with acetone (3×300 mL) with vortexing and sonication, and the solvent was evaporated under reduced pressure to afford an extract (149.2 mg). The extract was solubilized in MeOH (2 mL) and the material was subjected to solid phase extraction (SPE) (Waters Sep-Pak® Vac C18 cartridge, 35 cc (10 g)). The SPE cartridge was equilibrated with 10% MeCN/H$_2$O, and after loading the solvated extract, step gradient elution was performed by flushing the cartridge with 2×25 mL of the following MeCN/H$_2$O solvent mixtures: 10% (fractions 1 and 2), 25% (fractions 3 and 4), 50% (fractions 5 and 6), 75% (fractions 7 and 8), 100% (fractions 9 and 10), and the cartridge was then flushed with acetone (4×25 mL, fractions 11-14). Tartrolon D$_2$ was observed in fractions 10, 11, and 12. These fractions were consolidated and the solvent was evaporated under reduced pressure to afford a light yellow solid (35.5 mg). This material was then solvated in MeOH (3.5 mL) and passed through a syringe filter (0.2 µm) to remove particulate matter. The flow-through was subjected to semi-preparative HPLC on an Agilent Series 1100/1200 HPLC System equipped with a photo-diode array detector (DAD) using a Phenomenex Synergi™ 4 µm Hydro-RP 80 Å column (250×10 mm) employing isocratic elution with 95% MeCN/H$_2$O at a flow rate of 3 mL/min to obtain tartrolon D$_2$ as a white solid (3.5 mg, $t_R$=29.3 min).

The sample was analyzed via LC-MS, $^1$H NMR, and HRMS (performed on an Agilent 6350 QTOF mass spectrometer with a 1290 Infinity Binary LC), and then was dried and placed under high vacuum overnight before use in biological testing. LC-MS was performed on an Agilent Series 1200 HPLC System equipped with a photo-diode array detector (DAD) and a 6130 quadrupole mass spectrometer using an analytical Phenomenex Luna® 5 µm C18(2) 100 Å column (100×4.6 mm) with a linear gradient of 45%-90% MeCN+0.1% formic acid (FA)/H2O+0.1% FA over 20 min, then linear gradient to 100% MeCN+0.1% FA over 1 min, then isocratic MeCN+0.1% FA for 7 min, then linear gradient to 45% MeCN+0.1% FA over 1 min, then isocratic 45% MeCN+0.1% FA for 6 min all at a flow rate of 0.7 mL/min. Under these LC-MS conditions, tartrolon D$_2$ was found to have $t_R$=20.1 min.

For $^1$H NMR (500 MHz, CD$_3$OD): δ=6.12-6.02 (4H, m), 5.88 (2H, dt, J=14.4, 4.6 Hz), 5.30-5.25 (2H, m), 4.72-4.66 (2H, m), 4.49 (2H, s), 4.44-4.40 (2H, m), 3.99-3.95 (2H, m), 3.21 (4H, dd, J=18.3, 10.4 Hz), 2.63 (2H, dd, J=14.0, 3.9 Hz), 2.49-2.44 (4H, m), 2.42-2.33 (2H, m), 2.16-2.11 (2H, m), 2.04-1.90 (4H, m), 1.86-1.79 (2H, m), 1.78-1.65 (4H, m), 1.64-1.58 (4H, m), 1.44-1.38 (2H, m), 1.34-1.23 (4H, m), 1.16 (6H, d, J=6.1 Hz), 1.05 (6H, d, J=6.5 Hz), LRMS (ESI$^+$) m/z 843 [M+Na]; HRMS (ER$^+$) m/z calculated for C$_{44}$H$_{72}$NO$_{14}$ [M+NH$_4$]$^+$: 838.4953. Found: 838.4957.

The two preparations of Tartrolon D had identical anti-parasitic activity against *Toxoplasma gondii* (Example 6). It is henceforth concluded that the compounds of the invention prepared using either protocol have identical or comparable activity against different Apicomplexan species tested.

Example 5: In Vitro Effect of Purified Tartrolon D/E on *Toxoplasma gondii*

Readouts of host cell viability were used to quantify the dose-response of tartrolon D/E against *T. gondii*. Human foreskin fibroblast (HFF) cells, after having been infected by

Figure 4:
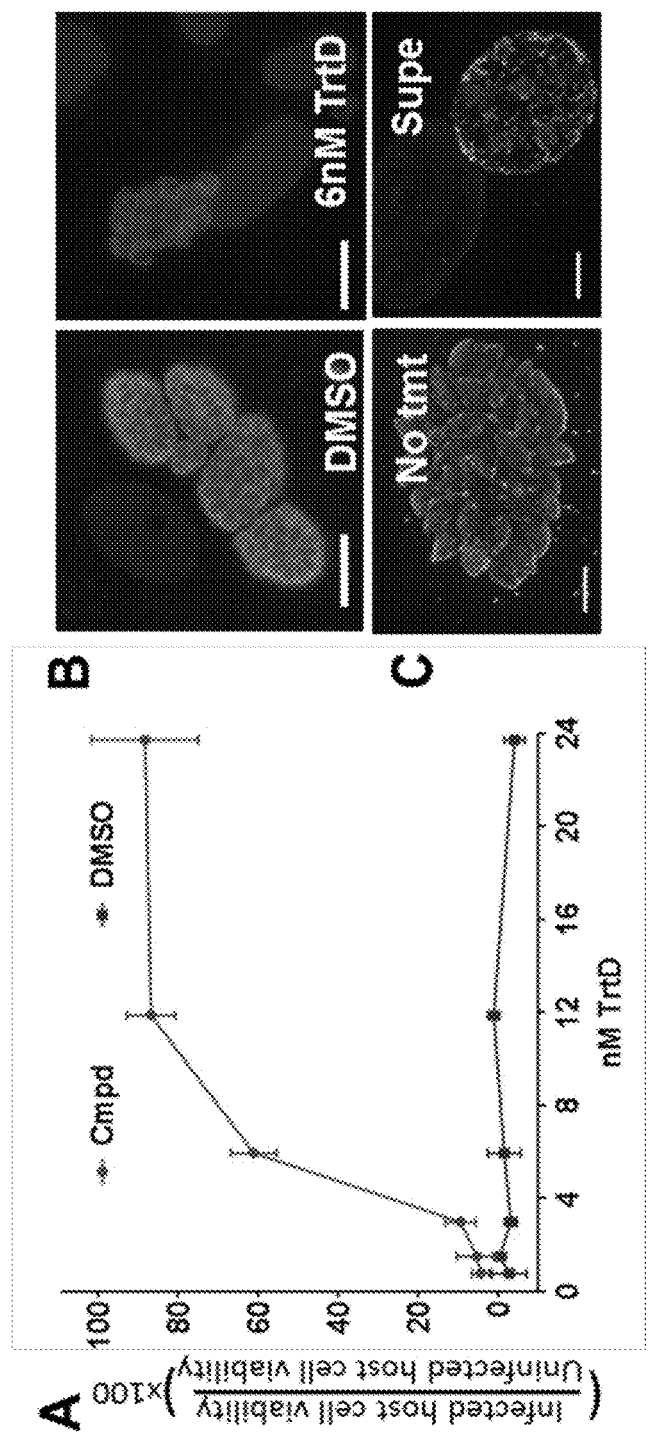
FIGS. 4A-4C illustrate data showing that the compounds of the invention inhibit intracellular proliferation of *T. gondii*: (4A) 3-(4,5-dimethylthiazol-2-yl)-5-(3-carboxymethoxyphenyl)-2-(4-sulfophenyl)-2H-tetrazolium (MTS assay) measuring host cell viability; (4B) Indirect immunofluorescence assay (IFA) of DMSO and tartrolon D/E treated parasites, visualized with anti-SAG1 primary antibody detected with Alexa flour 594 labeled goat anti-rabbit IgG (red) and the DNA stain 4',6-diamidino-2-phenylindole (DAPI) (scale=100 µm); (4C) IFA of untreated (left) and T7901 supernatant-treated (right) tachyzoites, visualized with anti-SAG1 primary antibody detected with Alexa flour 488 labeled goat anti-rabbit IgG (green) and DAPI, showing parasite nuclei in empty vacuole (scale=5 µm).

*T. gondii* for 24 hours, were treated with dilutions of tartrolon D/E that have been purified as in Example 2, or DMSO (control) for 72 hours. Host cell viability was then measured by MTS assay (CellTiter 96® AQ$_{ueous}$ One Solution Cell Proliferation Assay, Promega). The effective concentration at which 50% of the host cells survived (EC$_{50}$) was about 5 nM (FIG. 4A).

At the concentrations tested, tartrolon D/E had no effect on HFF cell viability as measured by MTS assay, indicating likely safety for in vivo administration. Tartrolon D/E-treated parasites exhibited an aberrant morphology in which parasite vacuoles contained intact parasite nuclei (FIG. 4C) but no distinguishable zoites (FIG. 4B). The aberration in the parasite morphology, stark when compared to untreated cell infection shown in the left columns of FIGS. 4B and 4C, provides direct evidence of irreversible inhibition and killing of the target parasite by compounds of the invention.

Example 6: Comparative Potency of Tartrolon D Preparations and their Activity Against a Clinically Relevant Strain of *Toxoplasma gondii*

Tartrolon D isolated using methods described above in Examples 3 and 4, respectively, yielded different preparations of the compound of the invention. The activity of both preparations against *Toxoplasma gondii* ME49, a type II strain, was assessed. Type II strains are responsible for many clinical cases of toxoplasmosis.

Human foreskin fibroblast (HFF) cells were established in 96-well plates, and then infected with ME49 parasites engineered to express green fluorescent protein and firefly luciferase (2.5 to 5×10$^5$/well). Eight hours after infection, dilutions of Tartrolon D$_1$ isolated as in Example 3, Tartrolon D$_2$ isolated as in Example 4, or vehicle (DMSO) at equivalent concentrations were added to infected cells and the plates incubated for 24 hours (37° C., 5% CO$_2$). Proliferation of the parasites was then measured using Bright-Glo luciferase assay system (available from Promega). Samples were run in triplicate and three independent biological replicates were conducted. The log 10 [Tartrolon D] versus percent inhibition of parasite proliferation was analyzed using the four parameter variable slope analysis in Graphpad Prism.

Figure 5:
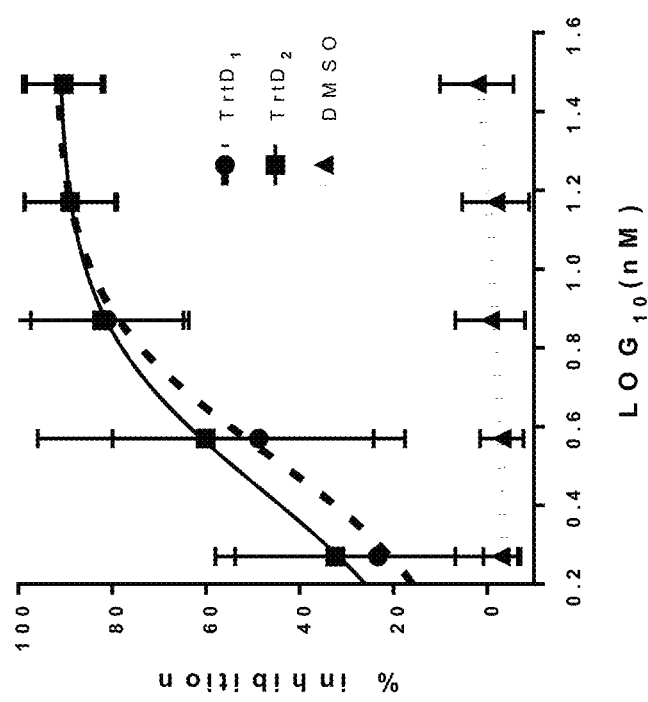
FIG. 5 illustrates equivalent efficacy against *Toxoplasma gondii* ME49 strain by two preparations of the compounds of the invention shown by direct measurement of parasitic proliferation using Bright-Glo luciferase assay. Using a four-parameter variable slope analysis of results averaged from 3 independent experiments, the $EC_{50}$ of tartrolon $D_1$ against *T. gondii* ME49 was calculated to be 3.4 nM and the $EC_{50}$ of tartrolon $D_2$, 2.7 nM.

Results are shown in FIG. 5. As can be seen, both preparations exhibited similarly strong potency against the parasite, as determined by direct measure of parasite proliferation. And both were effective at nM levels with EC$_{50}$ ranging from about 2.5 to 5.0 nM. For the specific samples presented in FIG. 5, The EC$_{50}$ was calculated to be 3.4 nM for Tartrolon D$_1$ and 2.7 nM for Tartrolon D$_2$.

Example 7: In Vitro Effect of Purified Tartrolon D/E on *Cryptosporidium parvum*

The effect of Tartrolon D/E on *Cryptosporidium* proliferation was evaluated by measuring host cell ATP levels (CellTiter-Glo® Luminescent Cell Viability Assay, Promega). Caco2 cells, having been infected with 2×10$^5$ *C. parvum* oocysts for 7 hours, were treated with dilutions of tartrolon D/E or DMSO (control) and cellular ATP levels were measured at the 48-hour time point post-infection.

Figure 6:
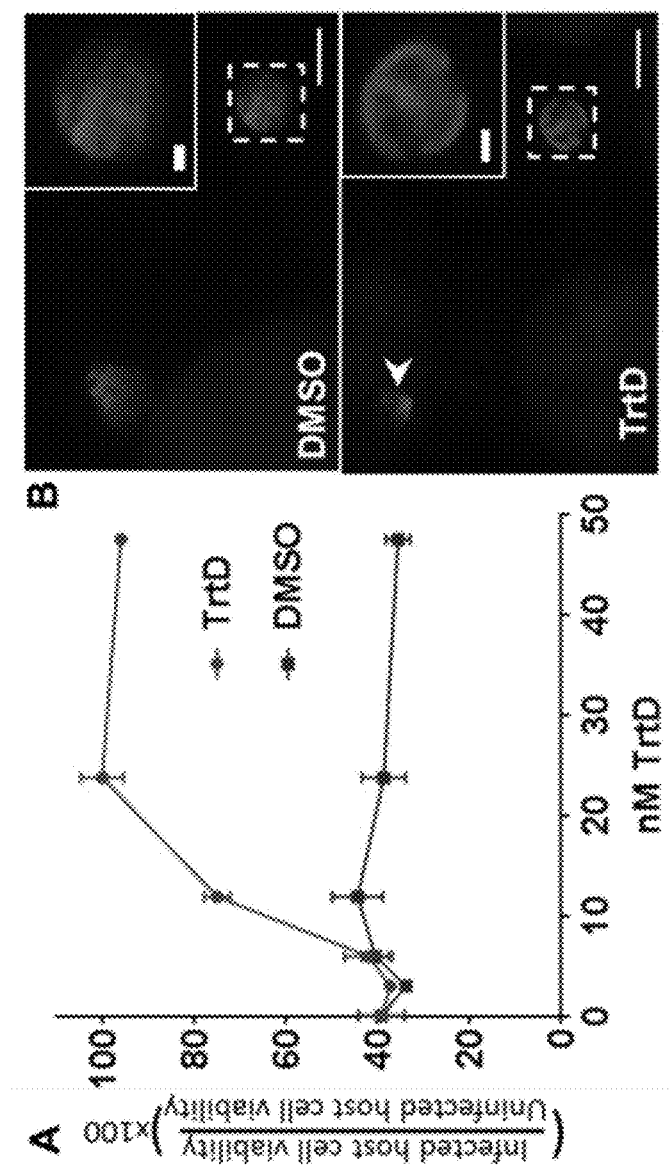
FIGS. 6A and 6B illustrate data showing that the compounds of the invention inhibit intracellular growth of *Cryptosporidium parvum*: (6A) Inhibition of *C. parvum* by tartrolon $D_1$ as measured by host cell viability using Adenosine triphosphate (ATP) assay; (6B) Morphology of *C. parvum* parasites after treatment with 100 nM tartrolon $D_1$ or DMSO for 9 hours. Insets (upper right in each image) are enlargements of boxed regions (dashes). Red: Rabbit α gp15 detected with Alexafluor 594-conjugated goat anti-rabbit IgG secondary antibody; blue: DAPI; scale=20 µm; insets=5 µm.

Based on host cell viability data, the EC$_{50}$ of Tartrolon D against *C. parvum* was about 12 nM (FIG. 6A). The morphology of treated parasites (FIG. 6B) was similar to that seen with *T. gondii*, in which the vacuole contained intact nuclei but no intact merozoites. In particular, most parasites did not progress past the single cell stage (lower panel, arrowhead); others never formed individual merozoites (lower panel, insets). Tartrolon D/E had no effect on Caco2 cell viability when added to cells at concentrations up to 500 nM, again suggesting a comfortable level of safety for in vivo administration.

Example 8: In Vitro Effects of Purified Tartrolon D/E on the Hemoparasite *Babesia bovis*

Purified tartrolon D/E (with starting materials being either D$_1$ or D$_2$) was tested against another apicomplexan pathogen, *Babesia bovis*, which proliferates in bovine red blood cells. Growth suppression of *B. bovis* was quantified using a modified SybrGreen-based assay (Molecular Probes, Life Sciences Technology). SYBR green is an asymmetrical cyanine dye that is used as a nucleic acid stain. In this assay, parasite replication in red blood cells is measured directly by the incorporation of SYBR green into parasite DNA. Tartrolon D/E concentrations ranging from 0.001 to 10,000 nM were tested on infected cells and DMSO (vehicle) was run in parallel as a negative control.

Figure 7:
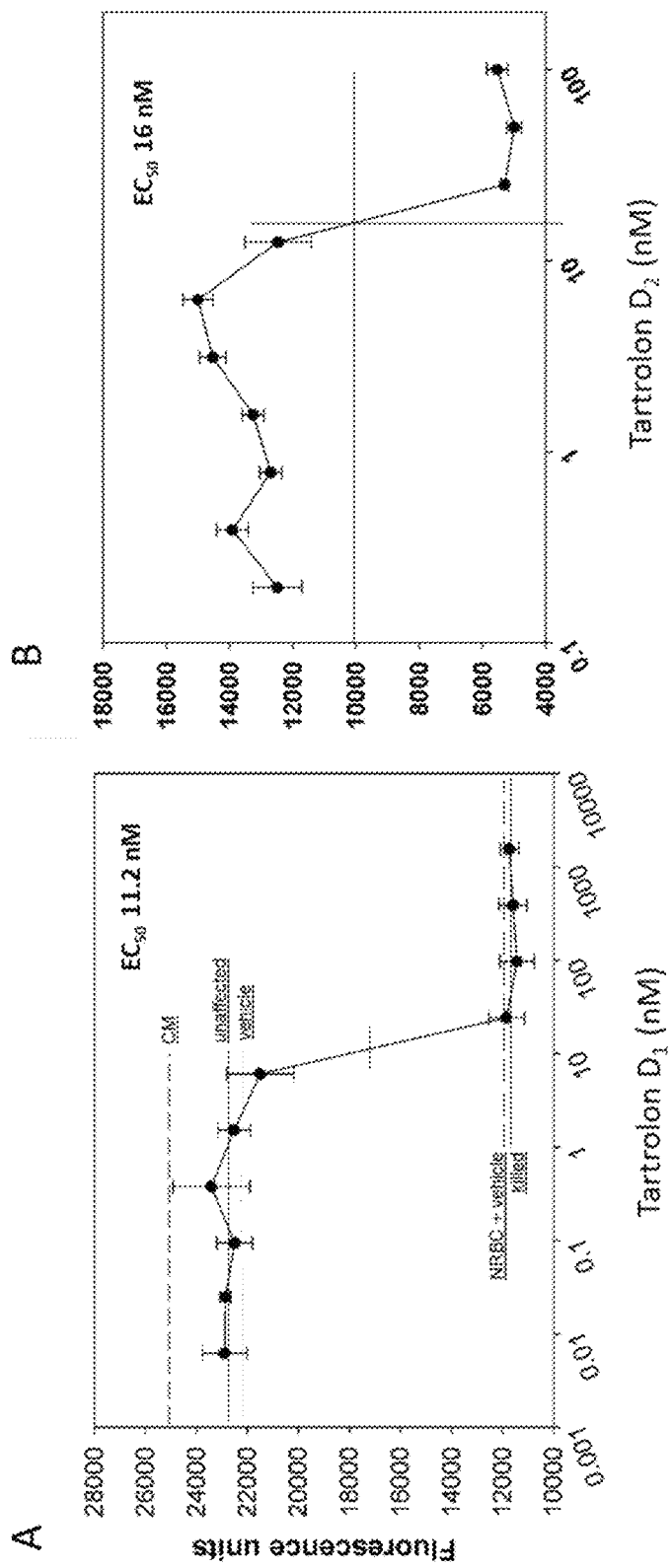
FIGS. 7A-7B illustrate in vitro data showing that the proliferation of *B. bovis* is inhibited by treatment with the compound(s) of the invention: (7A) tartrolon $D_1$ showed an $EC_{50}$ of 11.2 nM against *Babesia bovis*; and (7B) tartrolon $D_2$ showed an $EC_{50}$ of 16.0 nM against *Babesia bovis*. Inhibition was measured by optical readout of SYBR green fluorescence emitted by parasites in both figures.

FIGS. 7A and 7B show the fluorescence emitted by parasites that had incorporated the SYBR green dye. Based on the data, the EC$_{50}$ of tartrolon D$_1$/E against *B. bovis* was calculated to be 11.2 nM (FIG. 7A). Parasites treated with vehicle alone had no reduction in incorporated fluorescence, but parasites treated with more than 20 nM of tartrolon D$_1$/E did not incorporate any more fluorescence than uninfected red blood cells (NRBC). These results show that tartrolon D$_1$/E prevents proliferation of *B. bovis* and that the concentration at which 50% of the parasites are killed is about 11.2 nM. Similarly, the EC$_{50}$ of tartrolon D$_2$/E against *B. bovis* was calculated to be 16.0 nM (FIG. 7B), showing equivalent or comparable efficacy. In general, the compounds of the invention exhibited an EC$_{50}$ against *B. bovis* in the 11-16 nM range.

Example 9: Spectrum of Tartrolon D/E Activity

To determine the spectrum of inhibitory activity by the compounds of the invention against apicomplexan parasites, we tested tartrolon D$_2$ in in vitro assays against *Theileria equi, Sarcocystis neurona*, and *Plasmodium falciparum.*

*Theileria equi* is an apicomplexan hemoparasite of horses that causes equine piroplasmosis. While this parasite has been eradicated in the US, recent sporadic outbreaks have occurred, and the current available treatment is suboptimal. *Sarcocystis neurona* is an apicomplexan parasite that normally cycles between opossums and a range of intermediate hosts, but when it infects horses it causes a progressive neurological disease known as equine protozoal myeloencephalitis (EPM) for which there are no consistently effective treatments. *Plasmodium falciparum* is the etiological agent of severe malaria, a mosquito borne disease that kills approximately 700,000 to 800,000 people per year worldwide. This parasite's ability to rapidly develop resistance to anti-malarial drugs requires constant development of new and effective therapeutics to treat the infection.

*Theileria equi*: The effect of tartrolon D$_2$ on *T. equi* growth in vitro was quantified using an assay that has been previously described by Hines, S. A. et al. (Parasit Vectors 8, 33 (2015)). Briefly, wells containing an erythrocyte concentration of 9% and a starting percentage parasitized erythrocyte (ppe) of 0.3% were established in 96-well plates. Parasites were cultured in the presence of tartrolon D$_2$ or DMSO for 72 hours with a change of media and compound every 24 hours. After 72 hours, the parasites were stained with hydroethidine and enumerated by flow cytometry (FACSCaliber). Samples were run in triplicate and three independent experiments conducted. The data was analyzed and the $EC_{50}$ values calculated as described above for *T. gondii* ME49.

*Sarcocystis neurona*: Bovine turbinate cells (BT cells, ATCC CRL-1390, American Type Culture Collection, Manassas, Va.) were seeded into 96-well plates and infected with *S. neurona* merozoites that had been engineered to express green fluorescent protein and firefly luciferase ($2 \times 10^4$/well). Dilutions of tartrolon $D_2$ or DMSO were added to the infected cells and the plates incubated for 96 hours (37° C., 5% $CO_2$). After 96 hours, parasite proliferation was quantified and the data analyzed as described with *T. gondii* ME49. The assay was conducted once and all samples were run in triplicate.

*Plasmodium falciparum*: Parasites were cultured in 96-well plates at 0.5% initial parasitemia. Parasites were cultured for 72 hours in the presence of dilutions of tartrolon $D_2$, dihydroartemisinin (DHA, a drug for treating malaria as a positive control) or DMSO after which parasites were stained with SYBR green fluorescence and enumerated by flow cytometry. The assay was conducted once and all samples were run in triplicate. Data was analyzed with GraphPad Prism as described for *T. gondii*.

Figure 8:
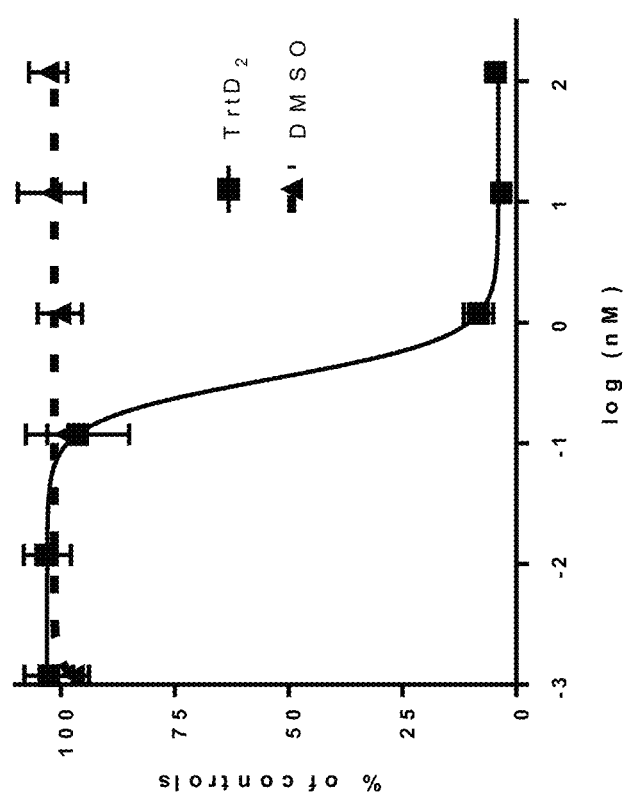
FIG. 8 illustrate in vitro data showing that the proliferation of *Theileria equi* is inhibited by treatment with the compound(s) of the invention with an $EC_{50}$ of about 0.35 nM. Results are averaged from three independent experiments.
Figure 9:
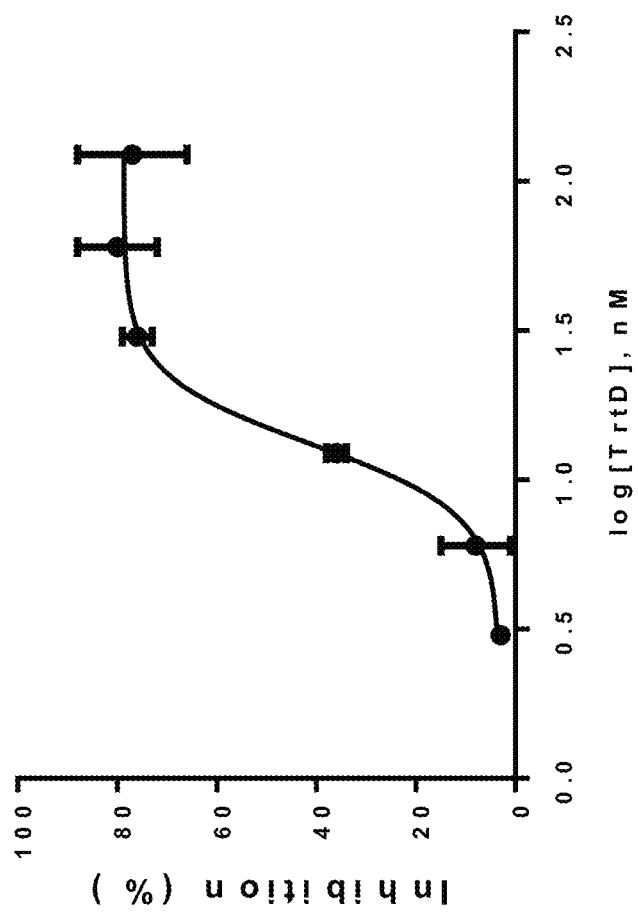
FIG. 9 illustrate in vitro data showing that the proliferation of *Sarcocystis neurona* is inhibited by treatment with the compound(s) of the invention with an $EC_{50}$ of about 13.2 nM.
Figure 10:
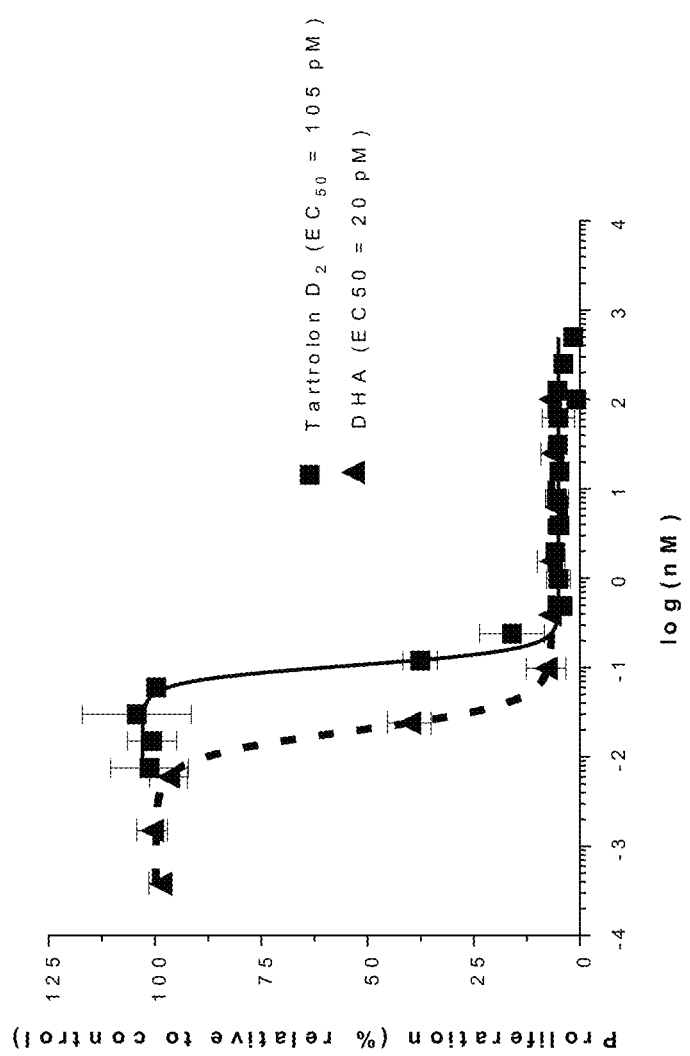
FIG. 10 illustrate in vitro data showing that the proliferation of *Plasmodium falciparum* 3D7 is inhibited by treatment with the compound(s) of the invention with an $EC_{50}$ of about 105 pM, where the $EC_{50}$ for the control dihydroartemisinin (DHA) is about 20 pM.

The results are depicted in FIGS. 8-10 and show that tartrolon D/E exhibits anti-parasitic activity against multiple apicomplexan parasites at low concentrations ranging from picomolar to nanomolar levels, provides further confidence that the tartrolon D/E, once administered in vivo, would likely achieve the expected anti-parasitic effects. In sum, tartrolon D/E (specifically, $D_2$) inhibited against proliferation of *Theileria equi* with an $EC_{50}$ of about 0.35 nM (FIG. 8, results averaged from three independent experiments), against the proliferation of *Sarcocystis neurona* with an $EC_{50}$ of about 13.2 nM (FIG. 9), and against the proliferation of *Plasmodium falciparum* (a drug-resistant strain, 3D7) with an $EC_{50}$ of about 105 pM (FIG. 10, also showing the $EC_{50}$ for the control DHA was comparable at about 20 pM).

Example 10: Experiments Testing the Potency of Tartrolon D/E Against Drug-Resistant Malaria Parasites Strains The potency of the compounds of the invention against multi-drug resistant *P. falciparum* strains was tested. Parasites were cultured in 96-well plates in human red blood cells at 0.5% initial parasitemia for 72 hours in the presence of dilutions of tartrolon D/E (specifically, $D_2$ as the starting material in FIG. 11A), purified tartrolon E (FIG. 11C), dihydroartemisinin (DHA, as a positive control in FIG. 11B), or DMSO (as a negative control). Parasites proliferation was then determined by $^3H$ hypoxanthine incorporation.

Specifically, parasitized red blood cells (pRBCs) were grown in 0.5% Albumax I (Thermo Fisher Scientific). Assays were set up in 96-well plates at 0.5% initial parasitemia and 0.5% hematocrit. Parasites were exposed to various concentrations of Tartrolon D or E and dihydroartemisinin (DHA) for 48 hours and then pulsed with 0.5 microcuries of tritium-labeled hypoxanthine Moravek (MT-700) for another 24 hours. At the end of 72 hours, assay plates were processed through an Inotech cell harvester and collected on Inotech glass fiber filters. Filters were transferred to Omniplate-96 cassettes (Perkin Elmer) and dried overnight at room temperature. About 25 mL of Microscint-O scintillation cocktail (Perkin Elmer) was added to each well. Each well was counted for 2 minutes on a Packard Topcount scintillation counter. The uptake of radiolabeled hypoxanthine by compound-treated pRBCs was compared relative to uptake by DMSO solvent-treated controls. Data at each concentration point were collected in triplicate and were fitted to the log[I] vs response-variable slope (4 parameter) model in Graph Pad Prism to determine the effective concentration of inhibitor that resulted in 50% growth inhibition. The starting material used as the active reagent in FIG. 11C was tartrolon E, purified as follows: extract from the bacterial pellet of the *Teredinibacter turnerae* T7901 was purified by reversed phase HPLC using diode array detection. A C18 column (Phenomenex CHO-7878, 100×10 mm) was employed with an isocratic mobile phase (85% acetontrile in water, 3.5 mL/min) to yield tartrolon E (4.7 mg, retention time 8 min).

Figures 11A, 11B:
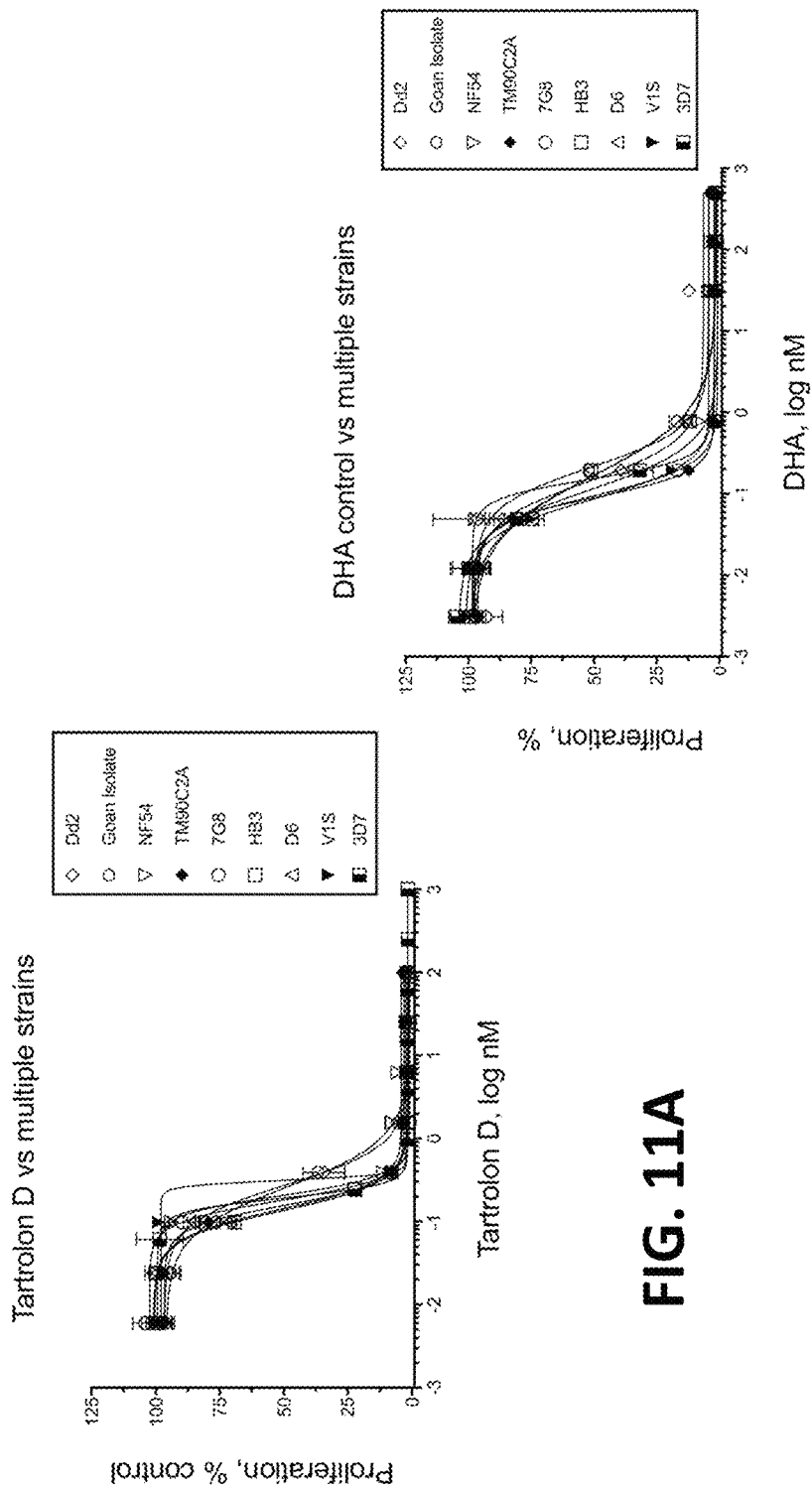
FIGS. 11A-11C illustrate data that show the potency of the compound(s) of the invention against multi-drug resistant strains of *Plasmodium falciparum*: (11A) multiple strains treated with Tartrolon D as a starting material; (11B) multiple strains treated with DHA; and (11C) multi-drug resistant strain Dd2 of *P. falciparum* treated with purified Tartrolon E as a starting material.
Figure 11C:
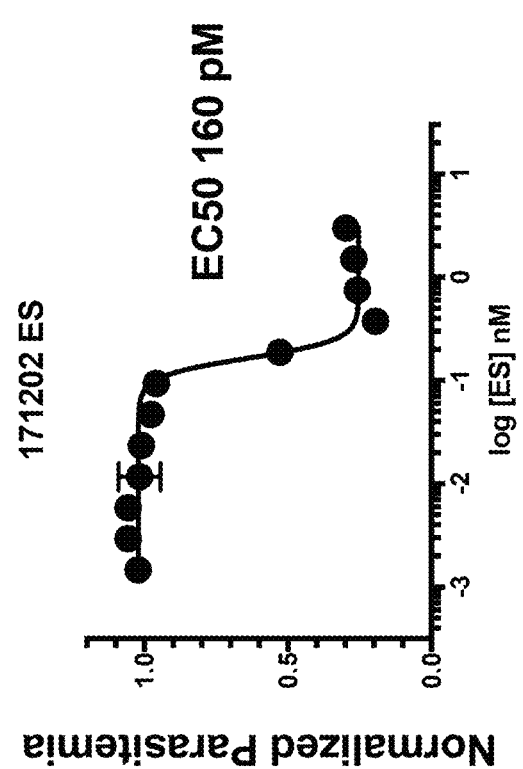

Results are presented in FIGS. 11A-11C. Table 1 summarizes the corresponding $EC_{50}$ values of tartrolon D as a starting material against each of the parasite strains. The $EC_{50}$ for tartrolon E as a starting material against one of these strains, Dd2, was about 160 pM (FIG. 11C).

TABLE 1

Ranked sensitivity to Tartrolon D/E of genetically distinct *Plasmodium* reference strains and a more recent Indian field isolate

| | $EC_{50}$, nM | |
|---|---|---|
| *P. Falciparum* parasite line | Tartrolon D | Dihydroartemisinin (DHA) |
| V1S | 0.31 | 0.084 |
| Dd2 | 0.28 | 0.14 |
| 2012 Indian Isolate (Goa) | 0.26 | 0.21 |
| NF54 | 0.20 | 0.15 |
| 7G8 | 0.18 | 0.095 |
| TM90C2A | 0.16 | 0.091 |
| D6 | 0.14 | 0.17 |
| HB3 | 0.13 | 0.16 |
| 3D7 | 0.11, 0.19 | 0.20, 0.11 |

The results showed that both clinical and highly drug-resistant *Plasmodium* strains are equally sensitive to the compound(s) of the invention. In particular, tartrolon D/E is highly potent against multi-drug resistant reference strains such as Dd2 and TM90C2A. Tartrolon D/E is also highly effective against more recently acquired field isolates such as one from Goa, India.

TABLE 2

Drug resistance phenotypes of isolates used

| No. | Cell Line | Origin | Chloroquine | Quinine | Mefloquine | Pyrimethamine | Sulfodoxine | Cycloguanil |
|---|---|---|---|---|---|---|---|---|
| 1 | Dd2 | SE Asia | R | R | R | R | R | R |
| 2 | Goan Isolate | Goa, India | R | Unknown | S | R | R | R |
| 3 | TM90C2A | Thailand | R | Unknown | R | R | Unknown | R |
| 4 | 7G8 | Brazil | R | R | S | R | Unknown | R |

TABLE 2-continued

Drug resistance phenotypes of isolates used

| No. | Cell Line | Origin | Chloroquine | Quinine | Mefloquine | Pyrimethamine | Sulfodoxine | Cycloguanil |
|---|---|---|---|---|---|---|---|---|
| 5 | V1/S | Vietnam | R | R | S | R | Unknown | R |
| 6 | HB3 | Honduras | S | S | S | R | S | S |
| 7 | NF54 | Netherlands | S | S | S | S | R | S |
| 8 | 3D7 | Netherlands (Clone of NF54) | S | S | S | S | R | S |
| 9 | D6 | Sierra Leone | S | S | S | S | S | S |

R = Clinically Resistant
S + Sensitive

Table 2 shows the drug resistance profiles of each of these strains. Resistance phenotypes of the *P. falciparum* strains used to test the effectiveness of Tartrolon D/E span a list of commonly used antimalarials. It is noted that pre-existing resistance to antifolates or aminoquinolines does not confer cross-resistance to Tartrolon D.

Example 11. Toxicity Test of Compounds of the Invention for Mammalian Cells

Figure 12:
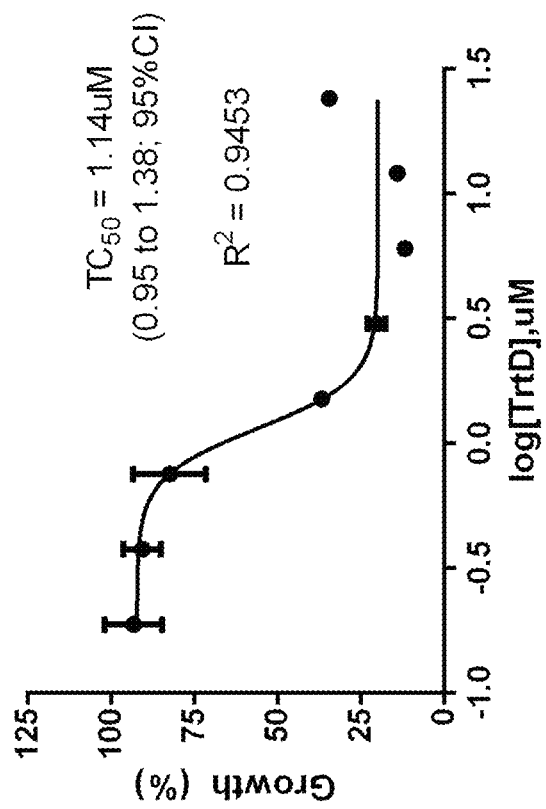
FIG. 12 shows toxicity test data of the compound(s) of the invention for Bovine Turbinate (BT) cells (ATCC #CRL-1390).

Toxicity of the compounds of the invention for mammalian cells was determined. Bovine Turbinate (BT) cells (ATCC #CRL-1390) are a primary cell line (not a transformed cancer cell line) and were used to provide a preliminary evaluation of the toxicity of tartrolon D/E for mammalian cells. Briefly, BT cells were cultured in the presence of increasing starting concentrations of Tartrolon D/E for 24 hours. Cell proliferation was measured using CellTiter Glo Cell Viability Assay (Promega) and the data was analyzed with GraphPad Prism. The results showed that the toxic dose at which 50% of the cells were killed was 1.14 µM (FIG. 12).

Example 12: In Vivo Effects on *Cryptosporidium parvum*

Figure 13B:
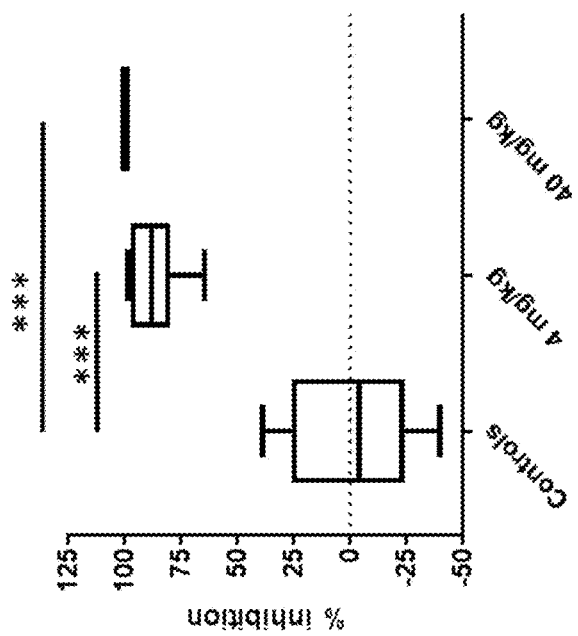
FIGS. 13A and 13B illustrate in vivo data that show the compound(s) of the invention inhibit *Cryptosporidium parvum*: (13A) Tartrolon $D_1$, as a starting material, inhibits *C. parvum* infections in neonatal mice; differences between groups were determined by Mann-Whitney t-test. Levels of infection were determined by counting parasites on histological sections of intestines from infected mice. Treatment started at the same time mice were infected. (13B) Tartrolon $D_2$, as a starting material, inhibits *C. parvum* infections in neonatal mice; Levels of infection were determined by quantitative PCR. Treatment was started 24 hours after infection (***$p<0.0001$). There was no significant difference between the high and low dose groups.
Figure 13A:
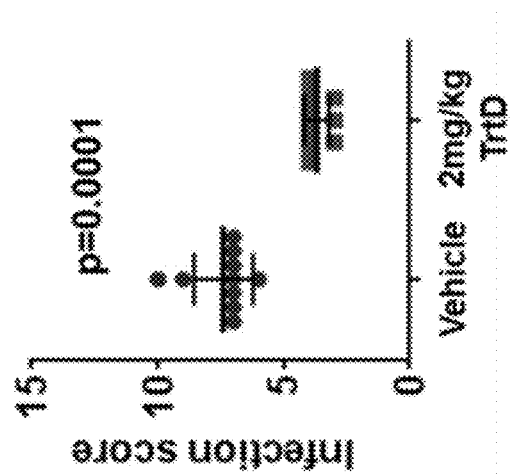

To determine if tartrolon D/E would be effective in vivo, the purified compound(s) of the invention was tested in a neonatal mouse model of *C. parvum* infection (Schaefer D A et al. (2000) *Infect Immun* 68(5):2608-261). Eight-day old neonatal mice were infected with *C. parvum* oocysts (50 times the $ID_{50}$) and treated with purified tartrolon D/E (specifically, $D_1$) or vehicle as a starting material for 4 days at 2 mg/kg/dose (b.i.d). At the end of the study period, mice were sacrificed and histological sections of jejunum, ileum, colon and caecum were examined. Infection in each section was scored by an observer blinded as to the sample identity. Despite the low dosage tested, infection was significantly inhibited by about 50% (FIG. 13A).

To confirm the in vivo activity against *Cryptosporidium parvum*, neonatal mice were infected with *C. parvum* ($5 \times 10^4$ oocysts per mouse), and 24 hours after infection, the mice were dosed twice daily for 4 days with either 4 or 40 mg/kg of tartrolon D/E (specifically, $D_2$) in starting concentrations. Day 5 post-infection, the mice were sacrificed, the intestines collected and total DNA extracted. Intestinal parasite numbers were quantified by quantitative PCR (qPCR) of the *C. parvum* HSP70 gene and extrapolation to a standard curve standard curve of known oocyst numbers (see Shahiduzzaman, et al., *Vet Parasitol* 167, 43-9 (2010)). At both the high and the low dose of Tartrolon D/E, nearly 100% of the parasites were eliminated from the intestine as measured by quantitative PCR. There was no significant difference between the groups receiving the high dose (40 mg/kg) and the low dose (4 mg/kg) of Tartrolon D/E. Both treated groups had significantly fewer parasites than the DMSO treated animals (p<0.0001). These data show that low doses of Tartrolon D/E are highly effective at eliminating *Cryptosporidium parvum* infection in neonatal mice (FIG. 13B).

Example 13: In Vivo Effects on *Plasmodium berghei*

Mice were infected with *Plasmodium berghei* expressing luciferase. 48 hours post infection mice were treated with tartrolon D/E (specifically, $D_2$) initially solubilized in 2% methylcellulose and 0.5% Tween80 by intraperitoneal injection for 5 days, once per day. Control mice were treated with vehicle alone. Seven days after infection, mice were given luciferase substrate (150 mg/kg D-luciferin Potassium salt in PBS (Goldbio)) and imaged in an IVIS Lumina II to quantify level of infection.

Results indicate that treatment with tartrolon D (specifically, $D_2$) as a starting material at 8 mg/kg reduced *P. berghei* infection in the mice. Specifically, in FIG. 14A, the graph shows the relative luminescence units emitted by each mouse (each individual mouse in FIG. 14B is represented by a respective circle or triangle in FIG. 14A with the same reference numbering). These data were analyzed in Graphpad PRISM by unpaired t-test and the difference between the vehicle-treated and the tartrolon-treated were within a significance at p=0.175.

In FIG. 14B, the picture shows the image of each mouse produced by the IVIS lumina. The greater the parasite numbers, the more intense the signal (as shown by color emission superimposed over the mice). For example, areas that indicated green, (see Ref No. 2) yellow (see Ref. No. 4) and red (see ref. No. 6) (as generally shown under the chins of mice 3 and 4) have the greatest numbers of parasites, The purple (e.g., see mouse 2, ref. No. 8 area) indicates moderate numbers of parasites; dark blue (e.g., see mouse 2, ref. No. 12 area) and light blue (e.g., see mouse 2, ref. No. 14 area) as shown in every image have low numbers of parasites. Importantly, areas that are white (i.e., as now denoted by white encircled areas in mice 3, 5, 7, 8 and 9), as shown in FIG. 14B, are areas in the mouse that have no parasites. As can be seen by comparing pictures of mice treated with vehicle and pictures of mice treated with tartrolon D/E, 4 of the 5 tartrolon-treated mice have significant areas with no parasites, whereas only 1 of the 4 control mice has a very small area without parasites.

These data show that treatment with the compound(s) of the invention, e.g., tartrolon D at a starting concentration of 8 mg/kg, reduced *P. berghei* infection in the mice.

While the present invention has been particularly shown and described with reference to the preferred embodiments disclosed herein and as illustrated in the drawings, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein. All publications and patent literature described herein are incorporated by reference in entirety to the extent permitted by applicable laws and regulations.

What is claimed is:

1. A method of treating or preventing a disease caused by an apicomplexan parasite in a subject in need thereof, comprising administering to the subject at least one of tartrolon D and E, in an amount that is therapeutically effective against the apicomplexan parasite.

2. The method of claim 1, wherein the at least one of tartrolon D and E has been purified.

3. The method of claim 1, wherein the apicomplexan parasite is a *Cryptosporidium* species.

4. The method of claim 1, wherein the apicomplexan parasite is *Toxoplasma gondii*.

5. The method of claim 1, wherein the apicomplexan parasite is a *Babesia* species.

6. The method of claim 5, wherein the apicomplexan parasite is *Babesia bovis*.

7. The method of claim 1, wherein the apicomplexan parasite is a *Plasmodium* species.

8. The method of claim 7, wherein the apicomplexan parasite is *Plasmodium falciparum* or *Plasmodium malariae*.

9. The method of claim 1, wherein the apicomplexan parasite is selected from the group consisting of *Cyclospora, Isospora, Eimeria, Sarcocystis, Theileria, Besnoitia, Hammondia*, and *Neospora*.

10. The method of claim 1, wherein the disease is cryptosporidiosis.

11. The method of claim 1, wherein the disease is toxoplasmosis.

12. The method of claim 1, wherein the disease is babesiosis.

13. The method of claim 1, wherein the disease is malaria.

14. The method of claim 1, wherein the disease is selected from the group consisting of cyclosporiasis, isosporiasis, sarcocystosis, besnoitiosis, hammondiosis, neosporiasis and theileriosis.

15. The method of claim 1, further comprising administering to the subject tartrolon D or E or both in a dose of at least about 2 mg for every kg of the subject's weight.

16. The method of claim 1, further comprising administering to the subject a second anti-parasitic agent against the same parasite.

17. The method of claim 1, further comprising administering to the subject both tartrolon D and E.

18. The method of claim 1, wherein the subject is selected from the group consisting of human, horse, sheep, goat, bovine, chicken, turkey, duck, goose, dog, cat, pig, rabbit, donkey, camels, llamas, alpaca, kangaroo, wallaby, lemur, birds, penguin, sea lion, seal, and sea otter.

* * * * *